(12) United States Patent
Tajima

(10) Patent No.: US 10,301,064 B2
(45) Date of Patent: May 28, 2019

(54) REACTION CONTAINER AND METHOD FOR PRODUCING SAME

(75) Inventor: Hideji Tajima, Matsudo (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 185 days.

(21) Appl. No.: 14/000,832

(22) PCT Filed: Aug. 19, 2011

(86) PCT No.: PCT/JP2011/068807
§ 371 (c)(1),
(2), (4) Date: Oct. 31, 2013

(87) PCT Pub. No.: WO2012/114562
PCT Pub. Date: Aug. 30, 2012

(65) Prior Publication Data
US 2014/0048540 A1      Feb. 20, 2014

(30) Foreign Application Priority Data

Feb. 22, 2011 (JP) .................................. 2011-003688

(51) Int. Cl.
| B65D 6/00 | (2006.01) |
| B01L 3/00 | (2006.01) |
| B01L 7/00 | (2006.01) |

(52) U.S. Cl.
CPC ............... *B65D 7/12* (2013.01); *B01L 3/523* (2013.01); *B01L 3/50855* (2013.01);
(Continued)

(58) Field of Classification Search
CPC ....... B65D 7/12; B01L 3/523; B01L 3/50825; B01L 2300/044
See application file for complete search history.

(56) References Cited

U.S. PATENT DOCUMENTS 4,683,202 A  7/1987  Mullis
5,958,349 A  9/1999  Petersen et al.
(Continued)

FOREIGN PATENT DOCUMENTS

EP  1541668 A1  6/2005
EP  2110670 A1  10/2009
(Continued)

OTHER PUBLICATIONS

International Search Report for PCT/JP2011/068807 by ISA/JP, and English translation, dated Sep. 13, 2011.
(Continued)

*Primary Examiner* — Matthew D Krcha
(74) *Attorney, Agent, or Firm* — Haynes and Boone, LLP

(57) ABSTRACT

The invention relates to a reaction container and a method for producing the reaction container, and provides a low-cost reaction container which is capable of consistently, quickly, and efficiently performing a process that includes a reaction such as extraction or amplification of a nucleic acid, while saving user's trouble without increasing the scale of the device.

The reaction container is configured to comprise: one or two or more housing parts for reactions comprising: a narrow-mouthed piping part in which a reaction reagent or a portion thereof is housed or is housable; a wide-mouthed piping part that is communicated with the narrow-mouthed piping part and provided on an upper side of the narrow-mouthed piping part, and has an aperture that is wider than an aperture of the narrow-mouthed piping part; and a punchable film provided such that it partitions an interval between the wide-mouthed piping part and the narrow-mouthed piping part.

19 Claims, 18 Drawing Sheets

(52) U.S. Cl.
CPC ............... *B01L 3/5635* (2013.01); *B01L 7/52* (2013.01); *B01L 2200/028* (2013.01); *B01L 2300/044* (2013.01); *B01L 2300/0832* (2013.01); *B01L 2300/1805* (2013.01); *B01L 2300/1822* (2013.01); *G01N 2201/0826* (2013.01)

(56) References Cited

U.S. PATENT DOCUMENTS

| | | | |
|---|---|---|---|
| 6,123,903 | A | 9/2000 | Tajima |
| 6,143,250 | A | 11/2000 | Tajima |
| 6,337,053 | B1 * | 1/2002 | Tajima .................. B01L 3/0275 422/553 |
| 2003/0062330 | A1 * | 4/2003 | Scalese ............... B01L 3/50825 215/354 |
| 2003/0162285 | A1 | 8/2003 | Tajima |
| 2004/0062688 | A1 * | 4/2004 | Guiles ................. B01J 19/0046 506/30 |
| 2005/0123457 | A1 | 6/2005 | Tajima et al. |
| 2006/0133965 | A1 | 6/2006 | Tajima et al. |
| 2007/0077655 | A1 * | 4/2007 | Unger .................... C12M 99/00 435/404 |
| 2007/0245810 | A1 * | 10/2007 | Carter ............... B01L 3/502723 73/53.01 |
| 2010/0291662 | A1 * | 11/2010 | Berner .................... B01L 3/508 435/283.1 |

FOREIGN PATENT DOCUMENTS

| | | | |
|---|---|---|---|
| JP | 08-211071 | A | 8/1996 |
| JP | 2007-178328 | A | 7/2007 |
| JP | 2007-189978 | A | 8/2007 |
| JP | 2007189978 | A * | 8/2007 |
| JP | 2010-094049 | A | 4/2010 |
| WO | WO 97/46712 | A2 | 12/1997 |
| WO | WO 2008/004695 | A1 | 1/2008 |
| WO | WO-2009095178 | A1 * | 8/2009 ............... B01L 3/508 |

OTHER PUBLICATIONS

Written Opinion for PCT/JP2011/068807 by ISA/JP, dated Sep. 13, 2011.
International Preliminary Examination Report for PCT/JP2011/068807, by IPEA/JP, dated Feb. 20, 2013.

* cited by examiner

REACTION CONTAINER AND METHOD FOR PRODUCING SAME

CROSS REFERENCE

This application is a United States national phase application of co-pending international patent application number PCT/JP2011/068807, filed Aug. 19, 2011, which claims priority to Japanese design application number 2011-003688D, filed Feb. 22, 2011, the disclosures of which are incorporated herein by reference.

TECHNICAL FIELD

The present invention relates to a reaction container and a method for producing the same.

BACKGROUND ART

Processing in which optical measurements are performed at the same time as reactions requiring temperature control, such as nucleic acid amplification or immunology at constant temperatures, is increasing in recent years. At the time amplification of nucleic acids (DNA, RNA, and the like) and the fragments thereof (oligonucleotides, nucleotides, and the like) is performed for example, in tests that require quantitativeness, such as the analysis of gene expression levels, it becomes necessary to perform the amplification such that the ratio of the relative amounts of the respective nucleic acids can be known. Consequently, by using the real-time PCR method, and by using a device provided with a thermal cycler and a fluorescence spectrophotometer, analysis by electrophoresis is made unnecessary as a result of the generation process of the DNA amplification products in PCR being detected and analyzed in real time. Furthermore, as a DNA amplification method that performs amplification while maintaining the quantitativeness with respect to the ratio of the relative amounts of the DNA or RNA contained in the sample before amplification, the SPIA (Single Primer Isothermal Amplification) method is used. In the SPIA method, the linear DNA amplification method resulting from an isothermal reaction utilizing DNA/RNA chimera primer, DNA polymerase, and RNaseH has become used.

The temperature control in such nucleic acid amplification involves housing a container, which is formed from polypropylene or the like and houses the necessary reagents, such as the template DNA, primers, DNA polymerase, nucleotides, and reaction buffer solutions, within a block-shaped housing part of an constant temperature device formed from a material such as aluminum, and by heating or cooling the metallic block-shaped housing part and waiting until the solution temperature becomes a uniform temperature distribution, it is made to perform heating or cooling at a constant temperature or at a next temperature (Patent Documents 1, 2 and 3).

At that time, the container for performing temperature control is sealed with a lid, preventing the entry of contaminants from the exterior, and preventing fluid leakage from the interior, and it is particularly necessary in order to exclude the effect of the air and the air temperature as much as possible until the reaction mixture within the housing part is heated or cooled, and the solution temperature becomes a uniform temperature distribution.

Then, in the real-time PCR method and the like, which monitors the nucleic acids (DNA, RNA, and the like) that are amplified in real time by utilizing a fluorescent compound, it is necessary to observe the amplification during a temperature cycle. Consequently, with respect to a container sealed with a lid, it is necessary to perform light measurements from the exterior through a transparent lid or side surface. However, the use of a lid and the manual opening of the lid by a user are time-consuming, and becomes an obstacle with respect to the consistent automation of processing. Furthermore, at the time the lid is resealed, there is a concern of contamination occurring from making contact with the reaction mixture in the container interior. Moreover, at the time of temperature control, even if the lid is attempted to be removed from the container, it is difficult to easily open the lid due to the lid becoming adhered to the container opening as a result of moisture, and there is a concern in that rapid processing cannot be performed. At the time the lid is opened, there is also a concern of contamination occurring from the liquid attached to the inside of the lid dripping or splashing (Patent Document 4).

Furthermore, at the time of temperature control, in a case where measurements of the interior of the container are performed from the exterior of the container, although there is a need to make the lid of the container transparent and to perform the measurements from the exterior, there is a concern of the interior of the lid becoming cloudy from condensation, and the measurements becoming difficult.

On the other hand, in order to perform processing such as nucleic acid amplification, as a precondition thereof, it becomes necessary to extract a small amount of nucleic acids from the sample and to perform processing within the reaction container together with various reagents, primers, DNA polymerase, nucleotides, reaction buffers, and the like, manually or using various devices for example. Therefore, in the present state, researchers and technicians that are specialized with regard to nucleic acids and the like are needed.

This situation is preventing the generalization of genetic analysis and the expansion of clinical applications in hospitals, and the like. Therefore, at the time of clinical use, and the like, in order to prevent cross-contamination and to reduce user labor, and to easily perform from the extraction, the amplification, and further, by means of a measurement, the genetic analysis of nucleic acids, then in addition to the need for full automation which consistently automates steps from the extraction, the amplification, and further up to the measurement of nucleic acids, the miniaturization of the device, and the provision of an inexpensive, high-accuracy device are important.

PRIOR ART DOCUMENTS

[Patent Document 1] Japanese Patent Publication No. 2622327

[Patent Document 2] Published Japanese translation No. 2000-511435 of PCT International Publication

[Patent Document 3] U.S. Pat. No. 5,958,349

[Patent Document 4] Japanese Unexamined Patent Publication No. 2002-10777

SUMMARY OF THE INVENTION

Problems to be Solved by the Invention

Therefore, the present invention is one that has been achieved in order to solve the problems mentioned above. A first object thereof is in providing a reaction container and a manufacturing method thereof wherein processing with a high reliability can be performed by preventing with certainty contamination due to the entry of contaminants from the exterior into the reaction container which performs reactions such as the amplification of nucleic acids in which temperature control is necessary, or splashing of liquids from the reaction container for example.

A second object is in providing a reaction container and a manufacturing method thereof that, at the very least, consistently automates processing including reactions, such as nucleic acid amplification, and optical measurements, reduces user labor, and can also be rapidly, efficiently, and inexpensively manufactured and utilized without expanding the scale of the device.

Means for Solving the Problem

A first aspect of the invention is a reaction container having one or two or more housing parts for reactions comprising: a narrow-mouthed piping part in which a reaction reagent or a portion thereof is housed or is housable; a wide-mouthed piping part that is communicated with the narrow-mouthed piping part and provided on an upper side of the narrow-mouthed piping part, and has an aperture that is wider than an aperture of the narrow-mouthed piping part; and a punchable film provided such that it partitions an interval between the wide-mouthed piping part and the narrow-mouthed piping part.

Here, the "reaction reagents or a portion thereof" represents the reagents used for a predetermined reaction or a portion of the reagents thereof, and can be housed in a liquid form or a dry state. In the case of a nucleic acid amplification reaction for example, the reaction reagent is a solution for amplification, and in a case where amplification is performed by the PCR method for example, it represents a template DNA solution which is the amplification subject, a primer solution, a DNA polymerase solution, a nucleotide solution, a reaction buffer solution, and the like. In a case where amplification is performed by the SPIA method, it represents a DNA/RNA chimera primer solution, a DNA polymerase solution, an RNaseH solution, and the like. Furthermore, generally, methods for performing real-time PCR using fluorescent reagents containing a fluorescent compound include the intercalation method, the hybridization method, and the LUX method. In the "intercalation method", a fluorescent compound such as SYBR (registered trademark) GREEN I or ethidium bromide, enters into double-stranded DNA at the time of the elongation reaction, and is a method in which the DNA amount is measured by irradiating an excitation light and utilizing the fluorescent light-emitting characteristics. Therefore, at the very least, the fluorescent material and a quencher that suppresses the light emission of the fluorescent material must be contained within the amplification solution. The "hybridization method" is a method that detects only a target PCR product by using a DNA probe labeled with a fluorescent material in addition to a PCR primer. That is to say, as a result of the DNA probe labeled by fluorescent light hybridizing with the target PCR product, the hybridized DNA (amount) thereof is detected. The "LUX method" is one that utilizes a property in which the fluorescent light signal of the fluorescent compound labeling the oligonucleotide is affected by the shape (such as a sequence, a single-strand, or a double-strand) of the oligonucleotide thereof. In actual real-time PCR, a PCR primer (LUX primer) that is labeled with one type of a fluorescent compound and a contrastingly unlabeled PCR primer are used to perform real-time PCR. The LUX primer thereof is labeled with a fluorescent compound in the vicinity of the 3'-terminus, and is designed such that it takes a hairpin structure in the interval between the 5'-terminus. When the LUX primer takes a hairpin structure, the quenching effect is resolved, and the fluorescent light signal becomes increased. By measuring this signal increase, the amount of the PCR product can be measured.

Examples of the material of the reaction containers, which includes the housing part for reactions, the lid, and the like, include resins such as polyethylene (P.E.), polypropylene (P.P.), polystyrene and acrylic, glass, metals, and metal compounds. The size of the reaction containers is such that the narrow-mouthed piping part is a size in which, in addition to several µL to several 100 µL of liquid being storable, the ends of the dispensing tips are insertable for example. In the case of a cylindrical shape, the diameter of the size of one reaction container is several mm to several 10 mm, and the depth is several mm to several 10 mm for example. The inner diameter of the wide-mouthed piping part is approximately 9 mm, the inner diameter of the aperture of the narrow-mouthed piping part is approximately 4 mm, the capacity of the narrow-mouthed piping part is approximately 50 µL, the liquid amount to be housed is approximately 25 µL, and the thickness is approximately 0.2 mm for example.

The interior of the reaction container is temperature controllable by means of a temperature controller.

The "temperature controller" has a temperature source that is able to raise or lower the temperature within the reaction containers which house the liquids that become subjected to temperature control, based on a signal from the exterior for example. The temperature source is one in which, for example, a Peltier element, a heater, a cooling device, and the like is provided on a block-shaped member. In order to perform processing such as PCR, the temperature controller is preferably a thermal cycler using a Peltier element. Furthermore, it is also possible to perform temperature control of an isothermal amplification by the LAMP method.

"Temperature control" represents, with respect to a liquid or a container that becomes the subject thereof, the maintaining of one or two or more set predetermined temperatures for set time periods, according to a specified sequence, and the execution at a specified frequency. The instructions to the temperature controller are carried out by sending a corresponding signal based on a program.

The "predetermined temperature" is a target temperature that an object, such as a liquid that becomes the subject, is to reach. In a case where nucleic acids, such as the DNA contained in the liquid, or oligonucleotides and the like, which represent fragments of nucleic acids, are amplified by the PCR method for example, the predetermined temperature that is set is a temperature cycle performed in the PCR method. That is to say, it represents temperatures that are respectively necessary for the denaturation, the annealing or the hybridization, and the elongation of DNA of approximately 94° C., a temperature in the interval from 50° C. to 60° C., and a temperature of approximately 72° C. for example. On the other hand, in the case of the SPIA method (trademark), it becomes set at a fixed temperature, such as 55° C. for example.

Furthermore, the predetermined temperature includes a temperature for transition acceleration that shortens the transition time and keeps the single cycle time within a predetermined cycle time as a result of, in the case of a transition from a high-temperature predetermined temperature to a low-temperature predetermined temperature, performing cooling at a temperature for transition acceleration that is lower than these predetermined temperatures by means of the temperature controller, or, at the time of a transition from a low-temperature predetermined temperature to a high-temperature predetermined temperature, by performing heating at a temperature for transition acceleration that is even higher than these predetermined temperatures for example. The "predetermined time" is the time necessary for maintaining the respective temperatures, and although it depends on the type of the amplification method, the amount of reagents, and the liquids used in the PCR method, and the shape, the material, the size, the thickness, and the like, of the nozzles, a single cycle is, in total, from several seconds to several 10 seconds for example, and the processing time for the PCR method as a whole is of the order of approximately several minutes to several 10 minutes for example. The transition time is also included in the predetermined time.

The punchable film includes aluminum foil for example. The punching is such that a tip for punching is mounted on a nozzle of a dispensing device used for dispensing liquids into the reaction container and provided on the outside of the reaction container, and punching is performed by positioning it above the reaction container and lowering it.

The "narrow-mouthed piping part" refers to a part in which the area of the aperture thereof is smaller than the aperture of the "wide-mouthed piping part". Preferably, the area of the aperture of the narrow-mouthed piping part is smaller than the area of the entire bottom portion of the wide-mouthed piping part. There is a case where the wide-mouthed piping part and the narrow-mouthed piping part are integrally formed, and a case where they are separately formed.

A second aspect of the invention is a reaction container in which the aperture of the narrow-mouthed piping part is provided at the center of a bottom portion of the wide-mouthed piping part.

Preferably, the wide-mouthed piping part and the narrow-mouthed piping part are formed with a rotation symmetry, and the wide-mouthed piping part and the narrow-mouthed piping part are coaxially formed. Since the aperture of the narrow-mouthed piping part represents the center of the bottom portion of the wide-mouthed piping part, the light from the narrow-mouthed piping part can be received with certainty along the axial direction of the wide-mouthed piping part. Furthermore, the "bottom portion" represents a wall surface that is formed such that it blocks the downward direction of the wide-mouthed piping part, and differs from the side portion that is formed such that it blocks the horizontal direction. Normally, it corresponds to a horizontal plane that is protrudingly provided in an inside direction from the inner wall surface of the wide-mouthed piping part, or a circular and stepped horizontal plane formed such that it narrows toward the downward direction. Therefore, even if the interval between the side portion of the wide-mouthed piping part and the side portion of the narrow-mouthed piping part is integrally formed, it is not uniformly and continuously joined, but is joined via the circular steps.

A third aspect of the invention is a reaction container having housing parts for reactions, wherein the narrow-mouthed piping part and the wide-mouthed piping part are integrally formed, and the film is attached to a bottom portion of the wide-mouthed piping part.

In this case, since the wide-mouthed piping part and the narrow-mouthed piping part are integrally formed, the construction is simple compared to a case where they are separately formed and assembled. On the other hand, the attachment operation of the punchable film is such that the film, which is cut beforehand according to the shape of the bottom portions of the wide-mouthed piping parts, is prepared, and following housing of the reaction reagents in the narrow-mouthed piping parts, it is necessary for them to be dropped in one at a time from the wide-mouthed piping part side and for them to be attached to just the bottom portions such that they do not make contact with the reaction reagents.

A fourth aspect of the invention is a reaction container comprising housing parts for reactions, wherein the wide-mouthed piping part and the narrow-mouthed piping part are separately formed; a hole portion is piercingly provided in the center of a bottom portion of the wide-mouthed piping part; the narrow-mouthed piping part has an aperture edge portion along an outer circumference of the aperture thereof and enclosing the aperture; the narrow-mouthed piping part is provided such that, excluding for the aperture edge portion, it is able to pass through the hole portion; the narrow-mouthed piping part downwardly protrudes from the hole portion of the wide-mouthed piping part such that it passes through the hole portion; the aperture edge portion is installed on the bottom of the wide-mouthed piping part; and the film is attached to the aperture edge portion of the narrow-mouthed piping part.

Here, the wide-mouthed piping part and the narrow-mouthed piping part are separately formed, and the punchable film is such that, following housing of the reaction reagents within the narrow-mouthed piping parts and after planarly arranging the plurality of narrow-mouthed piping parts, a large film is simultaneously attached to the aperture edge portions of the plurality of narrow-mouthed piping parts, and it can be collectively cut to match the aperture edge portions of the narrow-mouthed piping parts.

Thereafter, the narrow-mouthed piping part, to which the punchable film is attached to the aperture edge portion, is passed through further into the hole portion of the wide-mouthed piping part, and it is manufactured by mounting the aperture edge portion and the bottom portion of the wide-mouthed piping part such that there is no fluid leakage. The outer circumference length of the aperture edge portion is formed longer than the inner circumference length of the hole portion.

A fifth aspect of the invention is a reaction container further comprising a sealing lid, which has transparency, that seals the reaction container by being mounted on the aperture of the wide-mouthed piping part of the reaction container.

Here, the "sealing lid" includes, in addition to those that are inflexible and a plate form or block form, those that are a film form or a membrane form and have a flexibility. The "mounting" is performed by fitting, threading, friction, adsorption, attachment, adhesion, and the like. In this case, detachable mounting is preferable.

A single sealing lid seals the apertures of one or two or more reaction containers. The sealing lid is moved by being mounted on a nozzle mentioned below, and seals the apertures of the reaction containers using a tip detaching mechanism for example. This is achieved by providing on the upper side of the sealing lid, one or two or more cavities for mounting that are mountable to the one or two or more nozzles.

The one or two or more linking portions mentioned below are inserted into the cavities for mounting by a movement in the vertical direction of a light guide stage and can be linked with the reaction containers.

Furthermore, following linking of the respective linking portions of the light guide stage with the respective reaction containers, it is preferable to make the linking portions or the nozzles pressable or movable with respect to the sealing lid that cover the apertures of the reaction containers.

It is preferable for the linking portions to be provided such that they downwardly protrude from the light guide stage. In this case, it is preferable for the linking portions to have a shape such as a rod shape, a cylinder shape, or a cone shape, and for the lower end portions of the members to be able to make contact with the sealing lid for example.

A sixth aspect of the invention is a reaction container, wherein the sealing lid has: a plug portion that is fittable to the wide-mouthed piping part and is able to guide light from the narrow-mouthed piping part; and a pushing portion provided to an end of the plug portion that, in a case where the plug portion is fitted with the wide-mouthed piping part, pushes the film, which is insertable into the aperture of the narrow-mouthed piping part and is punched, into an inner wall of the narrow-mouthed piping part, and is also able to guide light from the narrow-mouthed piping part.

A seventh aspect of the invention is a reaction container as described in the first to sixth aspects, wherein the wide-mouthed piping part or sealing lid are provided such they are able to be linked with a linking portion provided with the ends of one or two or more light guide portions that optically connect a light measuring device provided on the exterior of the reaction container and the interior of the housing part for reactions.

Here, the "linking portion" is a member that is able to be releasably linked with the reaction container directly, or indirectly via the sealing lid and the like. Provided to the linking portion is the end of a light guide portion that is able to guide the light based on the optical state within the reaction container, by optically connecting with the interior of the reaction container. Here, the "linking with the reaction container" represents approaching or joining with the aperture, the outer wall, or the outer bottom portion of the reaction container or a mounted sealing lid or sleeve and the like. Furthermore, "approaching" represents, without making contact, an approach to an extent that optical connection of the interval with the light guide portions is possible. Moreover, "joining" includes making contact, close contact, adhesion, fitting, and mounting, and at the very least represents making contact such that optical connection of the interval between the light guide portions is possible. As a result of this linking, the light guide portion provided to the linking portion and the interior of the reaction container are optically connected. An example of the linking portion is a plate-shaped section of the light guide stage, and the end of the light guide portion is a hole piercingly provided in the plate-shaped section thereof, a transparent section such as an optical fiber, or an optical system such as a lens. Alternatively, for example, it is a member of a cylindrical shape, and the like, provided such that it protrudes from the light guide stage, and the end of the light guide portion is a cavity provided in the member of a cylindrical shape, and the like, a transparent section such as an optical fiber, or an optical system such as a lens. An example of a flexible light guide portion is an optical fiber or an optical fiber bundle. In a case where fluorescent light is measured, it has two or more light guide portions, and a portion thereof is for irradiation, and the others are used for receiving light. A case where it is directly linked with the aperture of the reaction container represents a case in which the interior of the reaction container is sealed using mineral oil and the like, and in this case, it is preferable to form the linking portion such that it is able to seal the reaction container. Furthermore, in a case where the linking is performed outside of the aperture, there is a need for the reaction container or the linking section thereof to have transparency.

Here, the "light guide stage" is described in relation to a fourteenth aspect of the invention mentioned below.

An eighth aspect of the invention is a reaction container, wherein the sealing lid has: a cavity provided in the center thereof; and a bottom surface, which has transparency, that blocks a lower end of the cavity, and movement of the sealing lid to the housing part for reactions, and the fitting and/or the linking with the linking portion, is performed by inserting a member provided on the exterior of the reaction container and/or the linking portion into the cavity.

Here, an example of the "member" includes a rod-shaped member dedicated to moving the sealing lids provided on the nozzle of the dispensing device or the nozzle head of the dispensing device that linkingly moves with the nozzle.

A ninth aspect of the invention is a reaction container that has a cartridge container which further has a base plate in which two or more concave portions are arranged in a single row form, and the housing part for reactions is formed in one of the concave portions, and in the other of the concave portions excluding the concave portion in which the housing part for reactions is formed, instruments for performing processing that are moved to the housing part for reactions are housed or are housable.

Here, examples of "processing" include dispensing with respect to the housing part for reactions, punching of the punchable film provided on the housing part for reactions, sealing and detaching of the sealing lid with respect to the housing part for reactions, and measurements relating to the solution housed in the housing part for reactions.

A tenth aspect of the invention is a reaction container, wherein the other concave portions excluding the concave portion in which the housing part for reactions is formed, are provided with a sealing lid housing part that houses the sealing lid, a tip for punching housing part that houses a tip for punching that punches the film, and/or a dispensing tip housing part that houses a dispensing tip.

An eleventh aspect of the invention is a reaction container, wherein the housing part for reactions is separately formed from the wide-mouthed piping part and the narrow-mouthed piping part, the wide-mouthed piping part is formed in the concave portion, a hole portion is piercingly provided in the center of a bottom portion of the wide-mouthed piping part, the narrow-mouthed piping part has an aperture edge portion that encloses the aperture thereof, the narrow-mouthed piping part downwardly protrudes from the hole portion of the wide-mouthed piping part such that it passes through the hole portion, the aperture edge portion is installed on the bottom portion of the wide-mouthed piping part, and the film is attached to the aperture edge portion of the narrow-mouthed piping part.

A twelfth aspect of the invention is a reaction container manufacturing method that separately manufactures a wide-mouthed piping part, to which a hole portion is piercingly provided in the center of a bottom portion, and a narrow-mouthed piping part that has an aperture edge portion that encloses the aperture along an outer circumference of the aperture, and manufactures a housing part for reactions by; housing, or not housing, a reaction reagent or a portion thereof within the narrow-mouthed piping part, attaching a punchable film to the aperture edge portion of the narrow-mouthed piping part, making the narrow-mouthed piping part downwardly protrude from the hole portion of the wide-mouthed piping part such that, excluding the aperture edge portion thereof, it is able to pass through the hole portion, and attaching the aperture edge portion to the bottom portion of the wide-mouthed piping part.

A thirteenth aspect of the invention is a reaction container manufacturing method that separately manufactures; a base plate in which two or more concave portions are formed, and in which a hole portion is piercingly provided in the center of a bottom portion of one of the concave portions, and a narrow-mouthed piping part that has an aperture edge portion that encloses the aperture along an outer circumference of the aperture, and manufactures a cartridge container by forming a housing part for reactions by housing, or not housing, a reaction reagent or a portion thereof within the narrow-mouthed piping part, attaching a punchable film to the aperture edge portion of the narrow-mouthed piping part, making the narrow-mouthed piping part downwardly protrude from the hole portion of the wide-mouthed piping part such that, excluding the aperture edge portion thereof, it is able to pass through the hole portion, and attaching the aperture edge portion to the bottom portion of the concave portion.

A fourteenth aspect of the invention is a reaction container system comprising: a nozzle head provided with a suction-discharge mechanism that performs the suction and the discharge of gases, and one or two or more nozzles that detachably mount dispensing tips, whereby the suction and the discharge of liquids is possible by means of the suction-discharge mechanism; a container group that has, at the very least, a reaction container described in any of the first to eleventh aspects whereby a solution for reaction, or a portion thereof, used for reactions is housed or is housable; a nozzle transfer mechanism that makes an interval between the nozzle head and the container group relatively movable; a temperature controller whereby temperature control of the interior of the reaction container is possible; a light guide stage provided to the nozzle head that has two or more linking portions that are directly or indirectly linkable with the housing part for reactions of the reaction container, to which the ends of one or two or more light guide portions that optically connect with the interior of the linked housing part for reactions are provided; a connecting end arranging body that has an arranging surface that supports two or more connecting ends that are provided corresponding to the respective linking portions and provided with a back end of the light guide portions, in which the ends thereof are provided to the linking portions, by arranging them along a predetermined path; a measuring device provided approaching or making contact with the arranging surface that, by means of optical connections with the respective connecting ends, is able to receive light based on an optical state within the reaction container; wherein the respective connecting ends provided along the predetermined path of the connecting end arranging body, and the respective measuring ends, mutually move such that they become successively optically connected.

The "predetermined path" represents, as a result of the measuring ends and the connecting end arranging body relatively moving, a path on a plane surface or a curved surface whereby the measuring ends are able to scan all of the connecting ends arranged therealong. Furthermore, the path that connects all of the connecting ends represents a single or multiple line segments that do not intersect (including zigzag lines and closed straight lines), curved lines (including spirals and closed curved lines), or a path along a combination of these and the like. Preferably, the respective single or multiple paths are continuous, and paths along line segments without cusps or corners, or smooth curves, are preferable.

There is a case where the linking portions and the connecting ends correspond one-to-one, a case where they correspond many-to-one, and a case where they correspond one-to-many. Here, midway, it is possible for the light guide portions to be branched or joined, or a light guide portion bundle comprising a plurality of light guide portions to be branched or joined.

It is preferable for the predetermined path to be determined based on the number, the shape, the arrangement, or the size of the measuring ends on the measuring device, such that smooth scanning is possible. For example, a predetermined path along a straight line in which, for the movement of the connecting ends with respect to the measuring ends, there are no sudden changes in direction, such as changes to an obtuse angle or a right angle direction with respect to the traveling direction, is preferable.

The arrangement pattern of the linking portions is a matrix form, a column form, or a row form for example. The arrangement pattern of the connecting ends is the same arrangement, or a similar arrangement that differs only in size for example, or in a case where the arrangement pattern is different, examples include the case of a circular form, other closed curved forms, a single column form, or a matrix form having a smaller number of columns or rows. The predetermined path is determined such that it passes through all of the arranged connecting ends.

Further, it is preferable for the predetermined path (or the arrangement pattern of the connecting ends) to represent a smaller region area or a smaller spacing than the region area that encloses the arrangement pattern of the linking portions on the light guide stage or the spacing between adjacent linking portions, and to be integrated such that the total scanning distance becomes short. Consequently, in a case where the speed is made the same, processing within a shorter time than a case where the linking portions directly scan the measuring ends is possible.

The extent of integration is preferably an extent in which the relative movement or scanning of the connecting end arranging body and the measuring device is able to complete the receiving of the light from all of the reaction containers to be measured within the stable light receivable time for example. Here, the "stable light receivable time" represents the time in which the optical state within the reaction containers, for which the light is receivable, is stably maintained. In the case of the intercalation method or the LUX method of real-time PCR, or the TaqMan probe of the hybridization method for example, it corresponds to the time in which the elongation reaction of the respective cycles of PCR is performed. In a case where a FRET probe is used in the hybridization method, it corresponds to the time in which annealing is performed.

Consequently, it can be applied with respect to a light emitter with a short stable light receivable time and the like, and the versatility is high.

If the time taken for a single cycle is made several 10 seconds or several minutes for example, the stable light receivable time becomes approximately several seconds to 10 seconds. However, the fluorescent light detection amount of the initial cycles of a PCR reaction is below the detection limit, and the later cycles of the PCR reaction become a plateau state, and in order to secure quantitativeness by a strict definition, it must be within a range of the amplification curve in which an exponential PCR amplification can be observed. The present invention is one in which the stable light receivable time utilizes the fact that the movement time of the measuring end between the reaction containers can be used, and by performing the relative movement necessary for receiving the light from the respective reaction containers within the stable light receivable time, the receiving of the light from the plurality of reaction containers can be performed approximately in parallel by means of a single measuring device, or a sufficiently small number in comparison to the number of reaction containers, without using a complicated optical system and without expanding the scale of the device.

The "optical state" represents a state such as light emissions, colors, color changes, or light variations. The light based on the optical state represents light from light emissions or light variations, or reflected light from light irradiated with respect to colors or color changes, or transmitted light, scattered light and the like.

The "connecting ends and the measuring ends are successively optically connected" represents that the connecting ends and the measuring ends are optically connected by becoming opposed at a close proximity. Since the amount of light received by the measuring device at the moment of connection corresponds to a maximum value, the measurement control portion specifies the data to be measured by calculating the maximum value of the amount of light.

The "measuring device" is one that makes fluorescence and chemiluminescence measurements possible for example, and in the former case, it has a filter for the irradiation of one or two or more types of excitation light and the receiving of fluorescent light having one or two or more types of wavelengths. It is preferable for these to be guided using an optical fiber.

The "measuring end" has, at the very least, an inlet for the light to be received provided to the measuring device, and in the case of a fluorescence measurement, has an outlet for the light to be irradiated. These can be provided as separate measuring ends. The inlet and the outlet are respectively optically connected to a light receiving portion comprising a photoelectric element and to an irradiation source, provided in the interior. At that time, they can be respectively connected via the light guide portion for receiving light and the light guide portion for irradiation.

The light measurement device for a reaction container, although not explicitly specified, additionally has "a measurement control portion". The "measurement control portion" controls the measuring device and a light guide switching mechanism, comprises a computer (CPU) built into the light measurement device for a reaction container and a program that drives the computer, and achieves measurement control by transmitting a signal through a DA converter to the respective control portions that drive the transfer mechanisms for example.

A fifteenth aspect of the invention is a reaction container system, wherein the container group additionally has: two or more liquid housing parts that house; a sample, a magnetic particle suspension in which magnetic particles that are able to capture a target substance of a reaction are suspended, and a solution for separating and extracting used for the separation and the extraction of the target substance; and a magnetic force part that is able to apply or remove a magnetic field to the interior of the dispensing tips mounted on the nozzles or the liquid housing parts provided to the container group, and which is able to adsorb the magnetic particles on an inner wall of the dispensing tips or the liquid housing parts.

EFFECTS OF THE INVENTION

According to the first aspect of the invention, the reaction container comprises a wide-mouthed piping part and narrow-mouthed piping part, a punchable film is provided such that it partitions the interval between the wide-mouthed piping part and the narrow-mouthed piping part, and a reaction reagent or a portion thereof is housed within the narrow-mouthed piping part. Therefore, splashing of the liquid at the time the film is punched or at the time of reaction processing can be prevented. Furthermore, at the time of linking of the linking portions and the wide-mouthed piping parts for guiding light over the interval with the optical measuring device, the light guide portions that pass through the interior of the linking portions are able to guide the light within the narrow-mouthed piping part to the measuring device with certainty.

According to the second aspect of the invention, since the aperture of the narrow-mouthed piping part is provided at the center of the bottom portion of the wide-mouthed piping part, at the time of linking with the linking portion, the light guide portion that passes through the interior of the linking portion is able to guide the light of the interior of the narrow-mouthed piping part to the measuring device with certainty. Furthermore, since the periphery of the bottom portion remains, this can be utilized to attach the film with certainty, or the separately provided narrow-mouthed piping part can be supported with certainty.

According to the third aspect of the invention, in addition to the effects of the first aspect of the invention, since the wide-mouthed piping part and the narrow-mouthed piping part are integrally formed, the molding is simple.

According to the fourth aspect of the invention, the eleventh aspect of the invention, the twelfth aspect of the invention, or the thirteenth aspect of the invention, the wide-mouthed piping part and the narrow-mouthed piping part are separately formed, and the punchable film is made to be attached to the aperture edge portion of the narrow-mouthed piping part, and after planarly arranging the plurality of narrow-mouthed piping parts, a large film is simultaneously attached to the aperture edge portions of the plurality of narrow-mouthed piping parts, and since it can be collectively cut to match the aperture edge portions of the narrow-mouthed piping parts, the film can be easily attached to the apertures of the narrow-mouthed piping part with certainty.

According to the fifth aspect of the invention, since a sealing lid, which has transparency, that seals the reaction container by being mounted on the aperture of the wide-mouthed piping part of the reaction portion is provided, temperature control and optical measurements can be performed with certainty.

According to the sixth aspect of the invention, since a pushing portion that pushes the punched film into the inner wall of the narrow-mouthed piping part is provided, a situation where the film blocks the guiding of the light is prevented, and measurements with a high reliability can be performed.

According to the seventh aspect of the invention, by means of the wide-mouthed piping part or the sealing lid linking with the linking portion provided to the end of the light guide portion, the light from a plurality of reaction containers can be successively guided to a single light measuring device without moving the light measuring device. Therefore, compared to a case where a light measuring device is provided to each reaction container, the scale of the device can be made compact.

According to the eighth aspect of the invention, the sealing lid is movable by utilizing the cavity thereof and by being mounted on members provided on the exterior of the reaction container, such as the nozzles, or the linking portion, and it is optically connectable with the light measuring device by linking with the linking portion. Therefore, the movement, the pressing, and the like, of the sealing lid is possible utilizing the dispensing device, and a compact device can be provided without providing new mechanisms.

The ninth aspect of the invention provides two or more concave portions arranged in a single row form with respect to the base plate of the cartridge container, and a housing part for reactions is provided to one thereof. Therefore, the punchable film is provided below the base plate surface, and cross-contamination from the splashing of liquids can be prevented with certainty at the time of punching, at the time of temperature control, and at the time of dispensing. Furthermore, since the movement of the dispensing tips and the like along the base plate surface is possible in a state where they are adjacent, then in addition to preventing cross-contamination, the movement control is easy.

In the tenth aspect of the invention, by providing the housing part for reactions, the sealing lid housing part, the tip for punching housing part, and the dispensing tip housing part to a single cartridge container in a single row form, then by utilizing the dispensing device, it becomes possible to execute the dispensing to the housing part for reactions, the punching of the punchable film, and the mounting of the sealing lid using the same nozzle. Furthermore, cross-contamination from the splashing of liquids is prevented, and an expansion in the scale of the device can be prevented.

According to the fourteenth aspect of the invention, as a result of linking with the plurality of reaction containers by means of the linking portions provided to the light guide stage and optically connecting with the interior of the reaction containers, the optical state within the reaction containers is transmitted via the plurality of reaction containers, the light guide stage, and the light guide portion, to the connecting ends of the arranging surface of the connecting end arranging body, and the connecting ends arranged along the predetermined path on the arranging surface of the connecting end arranging body and the measuring ends of the measuring device are successively optically connected. Therefore, compared to a case where the measuring ends are directly scanned with respect to the apertures of the reaction containers, then in addition to preventing the attenuation or the leakage of light from the scattering of light at the interval between the measuring ends and the liquid surface, the arrangement of the connecting ends is such that it can be rearranged in order to perform the connection with the measuring ends rapidly and smoothly, and with certainty. Therefore, measurements with a high reliability, and more efficient and rapid measurements of the optical state within the reaction containers, can be performed.

Consequently, with consideration of the stable light receivable time, the structure of the measuring ends, and the like, the arranging region of the connecting ends as a whole, or the distance between adjacent connecting ends can be achieved; by integration that makes the arranging region or the adjacent distances of the linking portions smaller, and, in comparison to the arrangement of the linking portion, by the smoothing of the movement of the measuring ends as a result of the linearization or the expansion of the radius of curvature of the predetermined path.

Switching of the optical system is performed by means of the movement between the measuring ends and the connecting ends on the arranging surface along the predetermined path. Therefore, the structure of the optical system can be simplified.

The movement of the connecting ends with respect to the measuring ends includes continuous or intermittent movement. As a result of the measurement by real-time PCR, an amplification curve is created, which can be utilized in various analyses, such as the determination of the initial concentration of DNA.

Moreover, since the measurement of the plurality of reaction containers can be performed in parallel with a single measuring device by utilizing the stable light receivable time, the expansion of the scale of the device is suppressed by reducing the number of measuring devices, and the manufacturing costs can be reduced. Further, since it is possible to measure, by successively moving the interval between the measuring ends and the connecting ends through the shortest distance along the predetermined path determined beforehand, the measurements can be performed in parallel by a simple mechanism of only a transfer mechanism.

In a case where the reactions and the measurements are performed by sealing the reaction containers by directly or indirectly linking the apertures of the reaction containers with the linking portions, automatic measurements with a high reliability in which cross-contaminations and the contamination of light can be prevented with certainty can be performed.

According to the fifteenth aspect of the invention, steps from the extraction of the target substance from the sample, to the housing in the housing part for reactions, temperature control (reaction), and the light measurement can be consistently and automatically performed in a single device without performing substitution of the containers belonging to the container group.

BEST MODE FOR CARRYING OUT THE INVENTION

Next, an embodiment of the present invention is described with reference to the drawings. This embodiment is not to be interpreted as limiting the present invention unless particularly specified. Furthermore, in the embodiments, the same objects are denoted by the same reference symbols, and the descriptions are omitted.

Figure 1:
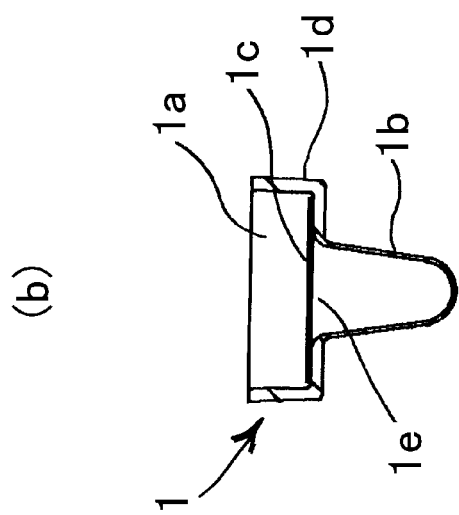
FIG. 1 is a drawing showing a housing part for reactions according to a first embodiment of the present invention.
Figure 1:
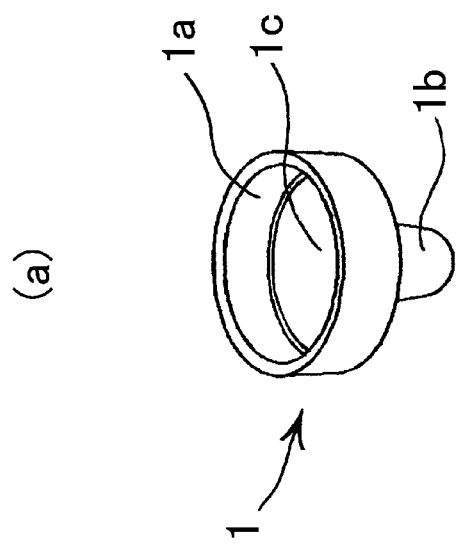

FIGS. 1(a) and 1(b) are drawings showing a housing part for reactions, which represents a reaction container, according to a first embodiment of the present invention.

The housing part for reactions 1 has: a narrow-mouthed piping part 1b, whereby a solution for nucleic acid amplification or a portion thereof, which represents the reaction reagent for nucleic acid amplification, is housable; a wide-mouthed piping part 1a that communicates with the narrow-mouthed piping part 1b, is provided on the upper side of the narrow-mouthed piping part 1b, and has a wider aperture than an aperture 1e of the narrow-mouthed piping part 1b; and a punchable film 1c formed from aluminum foil or the like, provided such that it partitions the interval between the wide-mouthed piping part 1a and the narrow-mouthed piping part 1b. By means of sealing the narrow-mouthed piping part 1b in an empty state with the film 1c, contamination of the narrow-mouthed piping part 1b can be prevented. The aperture 1e of the narrow-mouthed piping part 1b is provided at the center portion of a bottom portion 1d of the wide-mouthed piping part 1a. Furthermore, the narrow-mouthed piping part 1b and the wide-mouthed piping part 1a are integrally formed, and the film 1c is attached to the bottom portion 1d of the wide-mouthed piping part 1a.

Figure 2:
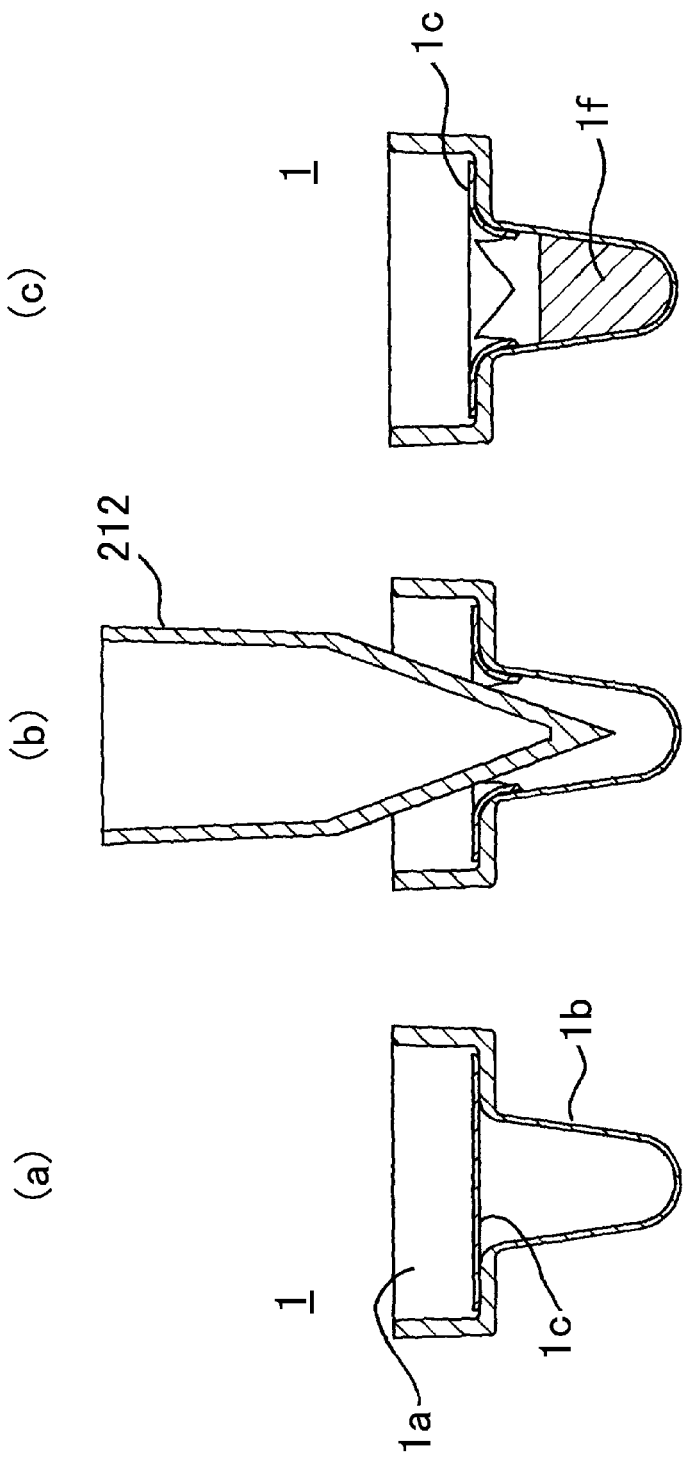
FIG. 2 is a processing explanatory drawing with regard to the housing part for reactions according to the first embodiment of the present invention.

FIG. 2 is a drawing showing the action in a case where, using a tip for punching 212 mounted on a nozzle head 50 mentioned below, the film 1c of the housing part for reactions 1 shown in FIG. 2(a) is punched, as shown in FIG. 2(b). FIG. 2(c) is a drawing showing a state in which a reaction reagent solution is housed following punching of the film 1c.

Figure 3:
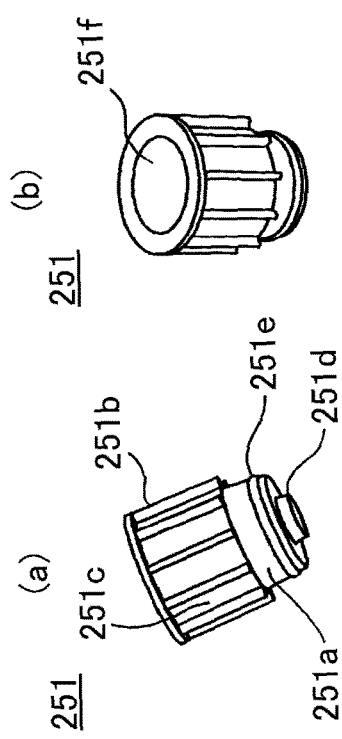
FIG. 3 is a drawing showing a sealing lid and the housing part for reactions according to the first embodiment of the present invention mounted with the same.
Figure 3:
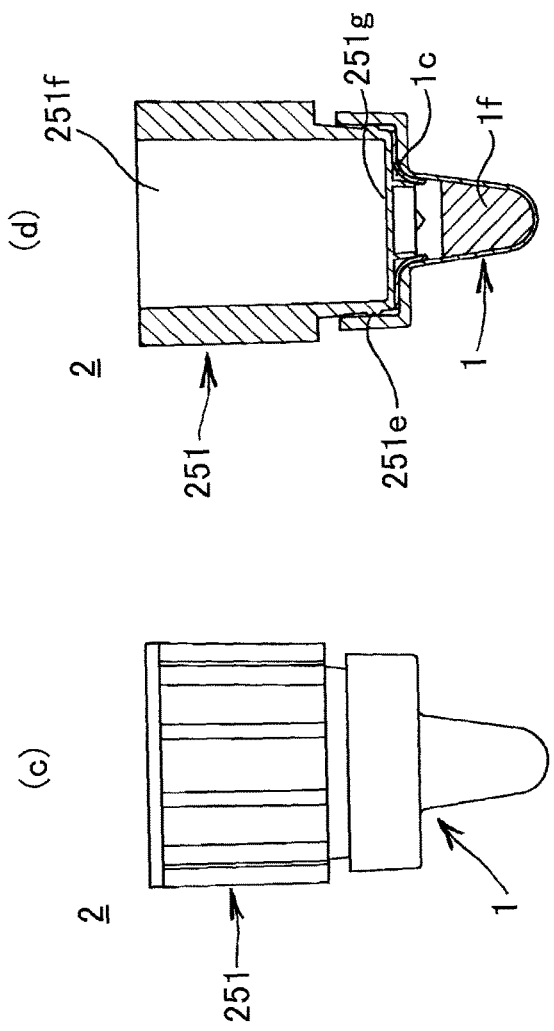

FIG. 3 is a drawing showing a reaction container 2 according to the first embodiment of the present invention, which comprises a lid 251 and a housing part for reactions 1 sealed by the lid 251.

As shown in FIG. 3(a) and FIG. 3(b), the sealing lid 251 which has transparency, has transparency, and has a plug portion 251 a that is fittable to the aperture of the wide-mouthed piping part 1a, and a cylindrical member 251c provided on the upper side of the plug portion 251a and on which a plurality of protrusions 251b along the axial direction are arranged on the outside surface. Furthermore, the plug portion 251a is provided with a circular protrusion 251e that protrudes along the outer circumference thereof in the radial direction, and adheres to the inner wall of the wide-mouthed piping part 1a. The lower side of the plug portion 251a is provided with a pushing portion 251d that is inserted into the aperture of the narrow-mouthed piping part 1b, and pushes the punched punchable film 1c into the rim of the aperture.

Figure 4:
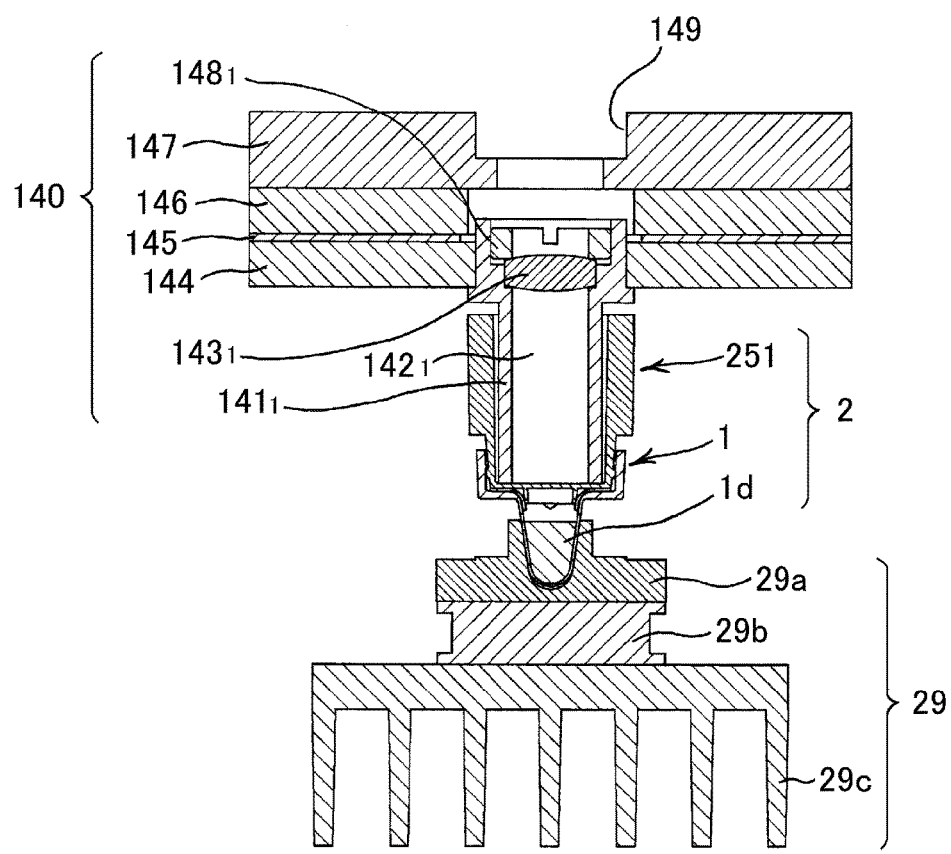
FIG. 4 is a drawing in which a linking portion is linked with the housing part for reactions according to the first embodiment of the present invention.

As shown in FIG. 4, the reaction containers 2, which comprise a housing part for reactions 1 sealed by the sealing lid 251, are further respectively housed in a plurality of indentations arranged in a single row form (front-to-rear direction in the drawing) of a block 29a of a temperature controller 29 that performs the temperature control necessary for nucleic acid amplification reactions. The block 29a is heated and cooled by means of a Peltier element 29b and a heat sink 29c. The upper side of the housing parts for reactions 1 is provided with a light guide stage 147 that is mounted such that a single measuring device moves and is able to successively optically connect with the plurality of housing parts for reactions 1. Furthermore, a plurality of linking portions 141, are provided such that they downwardly protrude from the light guide stage 147 in a single row form (front-to-rear direction in the drawing). The respective linking portions 141 are inserted into a cavity 251f (see FIG. 3) of the respective sealing lids 251, and since the light guide portions 142 that pass through the interior of the linking portions 141 have a size that approximately covers the apertures of the narrow-mouthed piping parts 1b, the light within the narrow-mouthed piping part 1b can be guided with certainty via the light guide portion 142 to the measuring device on the light guide stage 147 without loss. Consequently, by utilizing the stable light receivable time of the fluorescence, and the like, that is generated at the time amplification reactions of nucleic acids (DNA, RNA and the like) and the fragments thereof (oligonucleotides, nucleotides and the like) are performed using the real-time PCR method, and by moving a single measuring device, measurements relating to the plurality of housing parts for reactions 1 are made possible, and the overall device construction can be made compact. Reference symbol 143 is a lens, reference symbol 144 is a hot lid, reference symbol 145 is a seat heater, reference symbol 146 is a heat insulator, and reference symbol 148 is a pressing ring of the lens, and the prevention of condensation of the sealing lid, which is a sign of the nucleic acid amplification reaction, is achieved as a result of these. Furthermore, the groove 149 provided in the light guide stage 147 is one that guides the movement (front-to-rear direction in the drawing) of the measuring device such that the measuring device becomes successively connectable with the light guide portions 142 that correspond to the respective housing parts for reactions 1.

Figure 5:
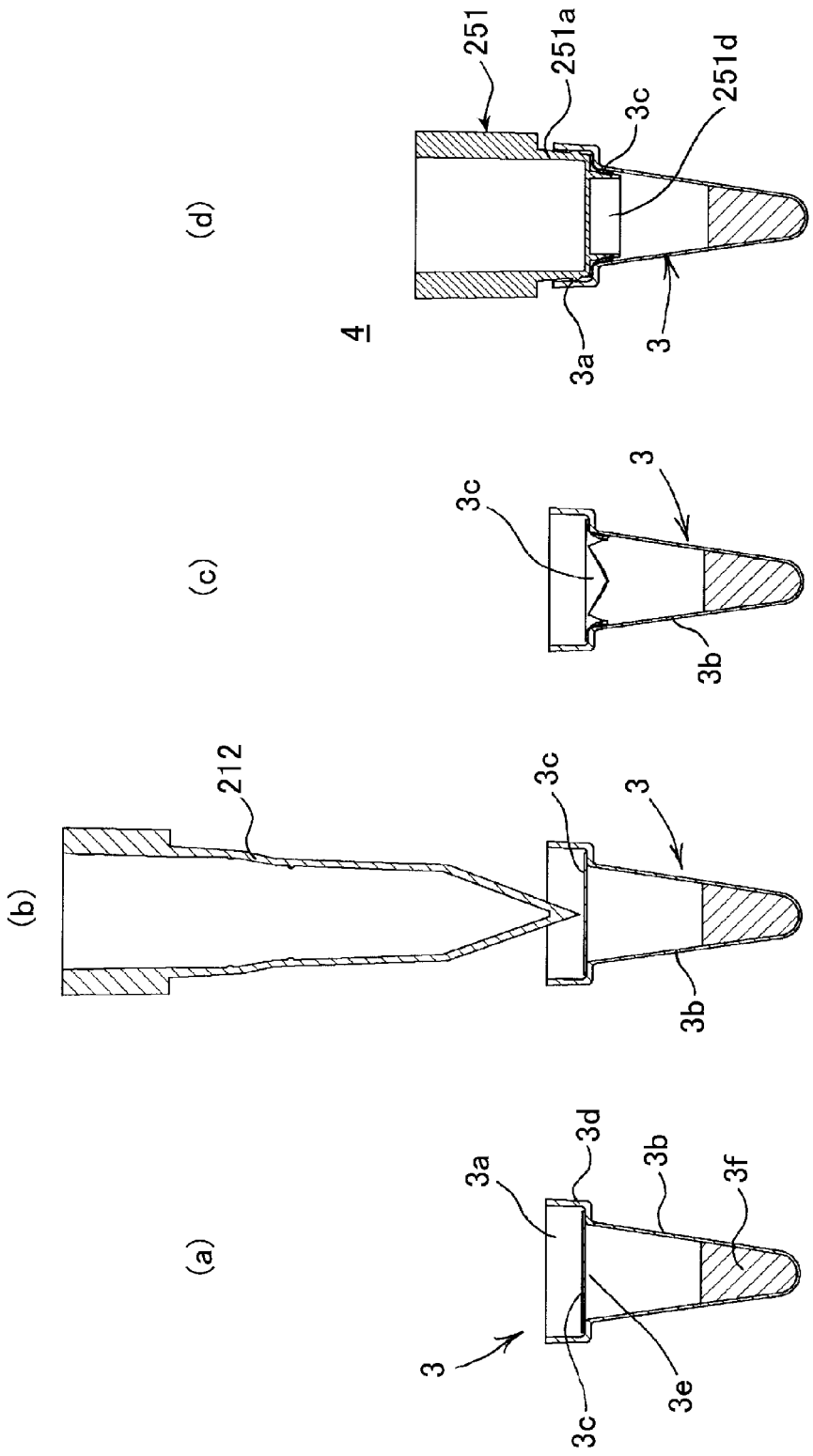
FIG. 5 is a housing part for reactions according to a second embodiment of the present invention, and a processing explanatory drawing thereof.

FIG. 5 is a housing part for reactions 3 according to a second embodiment of the present invention, and a processing explanatory drawing thereof.

As shown in FIG. 5(a), the housing part for reactions 3 according to the second embodiment has: a narrow-mouthed piping part 3b whereby a solution for nucleic acid amplification or a portion thereof 3f, which represents the reaction reagent for nucleic acid amplification, is housed beforehand; a wide-mouthed piping part 3a that communicates with the narrow-mouthed piping part 3b, is provided on the upper side of the narrow-mouthed piping part 3b, and has a wider aperture than an aperture 3e of the narrow-mouthed piping part 3b; and a punchable film 3c formed from aluminum foil or the like, provided such that it partitions the interval between the wide-mouthed piping part 3a and the narrow-mouthed piping part 3b. By means of sealing the narrow-mouthed piping part 3b with the film 3c, evaporation or contamination of the reagent housed within the narrow-mouthed piping part 3b can be prevented. The aperture 3e of the narrow-mouthed piping 3b is provided at the center portion of a bottom portion 3d of the wide-mouthed piping part 3a. Furthermore, the narrow-mouthed piping part 3b and the wide-mouthed piping part 3a are integrally formed, and the film 3c is attached to the bottom portion 3d of the wide-mouthed piping part 3a.

FIG. 5(b) is a drawing showing a state in which, in order to punch the film 3c of the reaction housing part 3 shown in FIG. 5(a) using the tip for punching 212 mounted on the nozzle head 50 mentioned below, it is positioned on the upper side thereof. FIG. 5(c) is a drawing showing a state in which, by lowering the tip for punching 212, the end is inserted into the narrow-mouthed piping part 3b, and the film 3c is punched. FIG. 5(d) is a drawing showing a reaction container 4 comprising; a sealing lid 251 exhibiting a state in which the plug portion 251a of the sealing lid 251 is fitted within the wide-mouthed piping part 3a of the housing part for reactions 3, in which the film 3c has been punched, and the film 3c that has been punched is pushed into the inner wall of the aperture of the narrow-mouthed piping part 3b by the pushing portion 251d provided on the end of the plug portion 251a, and the housing part for reactions 3.

Figure 6:
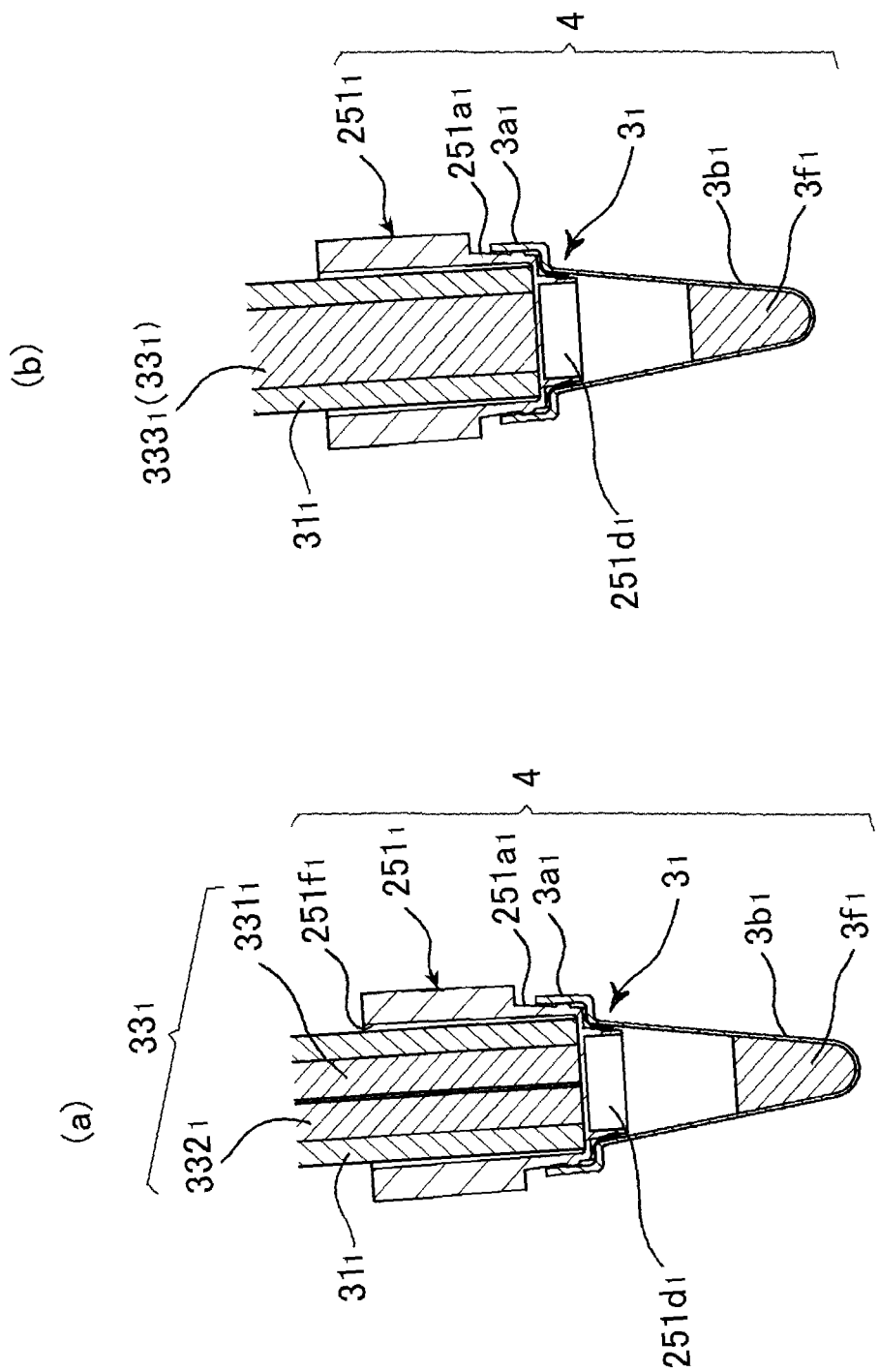
FIG. 6 is a drawing in which a linking portion is linked with the housing part for reactions according to the second embodiment of the present invention.

FIG. 6(a) and FIG. 6(b) are drawings showing a case where a linking portion $31_1$ is linked with the housing part for reactions 3 according to the second embodiment of the present invention.

The plug portion $251a_1$ of the sealing lid 251 is fitted with the wide-mouthed piping part 3a of the housing part for reactions 3, which has a punched film $3c_1$, and the film $3c_1$ exhibits a state in which it is pushed into the inner wall of the narrow-mouthed piping part $3b_1$ by means of the pushing portion $251d_1$. Further, it exhibits a state in which the linking portion $31_1$ mentioned below is inserted into the cavity $251f_1$ of the sealing lid $251_1$.

FIG. 6(a) is a drawing showing a state in which the linking portion $31_i$ (here, i=1 for example) that downwardly protrudes from the horizontal plate 32a of the light guide stage 32 mentioned below, is indirectly linked with the housing part for reactions 3 via the sealing lid $251_i$ which has transparency, that is mounted on the wide-mouthed piping part $3a_i$ of the housing part for reactions 3, and the linking portion $31_i$ is inserted into the cavity of the sealing lid $251_i$, and the end surface thereof is adhered to the bottom surface of the cavity of the sealing lid $251_i$. The housing part for reactions $3_i$ comprises a wide-mouthed piping part $3a_i$, and a narrow mouthed piping part $3b_i$ communicated with the wide-mouthed piping part $3a_i$ and formed narrower than the wide-mouthed piping part $3a_i$. Furthermore, the narrow-mouthed piping part $3b_i$ is dried beforehand, or a liquid state solution for amplification $3f_i$ is housed beforehand. Here, the reagent for real-time amplification represents 70 μL of a master mix (SYBR (registered trademark) Green Mix) consisting of enzymes, buffers, primers, and the like.

For the aperture of the wide-mouthed piping part $3ai$, in order to mount the sealing lid $251_i$ which has transparency and protrudes on the lower side of the sealing lid $251_i$, onto the housing part for reactions $3_i$, and as a result of the circular pushing portion $251d_i$ which encloses the center portion in which the light of the sealing lid $251_i$ passes through, being inserted into the narrow-mouthed piping part, it is preferable for the diameter of the optical fiber (bundle) $33_i$ which represents the light guide portion that passes through the linking portion $31_i$, to be the same or larger than the diameter of the aperture of the narrow-mouthed piping part $3b_i$. Consequently, it becomes possible to receive the light from the housing part for reactions $3_i$ with certainty. The narrow-mouthed piping part $3b_i$ is housed within a block for temperature control that is heated or cooled by means of the temperature controller 29.

In this example, the optical fiber (bundle) $33_i$ comprises an optical fiber (bundle) for irradiation $332_i$ that is connectable with a second measuring end $43_i$, and an optical fiber (bundle) for receiving light $331_i$ that is connectable with a first measuring end $42_i$.

FIG. 6(b) is a drawing showing an example in which the optical fiber (bundle) $33_i$ comprises an optical fiber bundle in which an optical fiber bundle comprising a plurality of optical fibers for receiving light that are connectable with the second measuring end $43_i$, and an optical fiber bundle comprising a plurality of optical fibers for irradiation that are connectable with the first measuring end $42_i$, are combined such that they become uniform.

Figure 7:
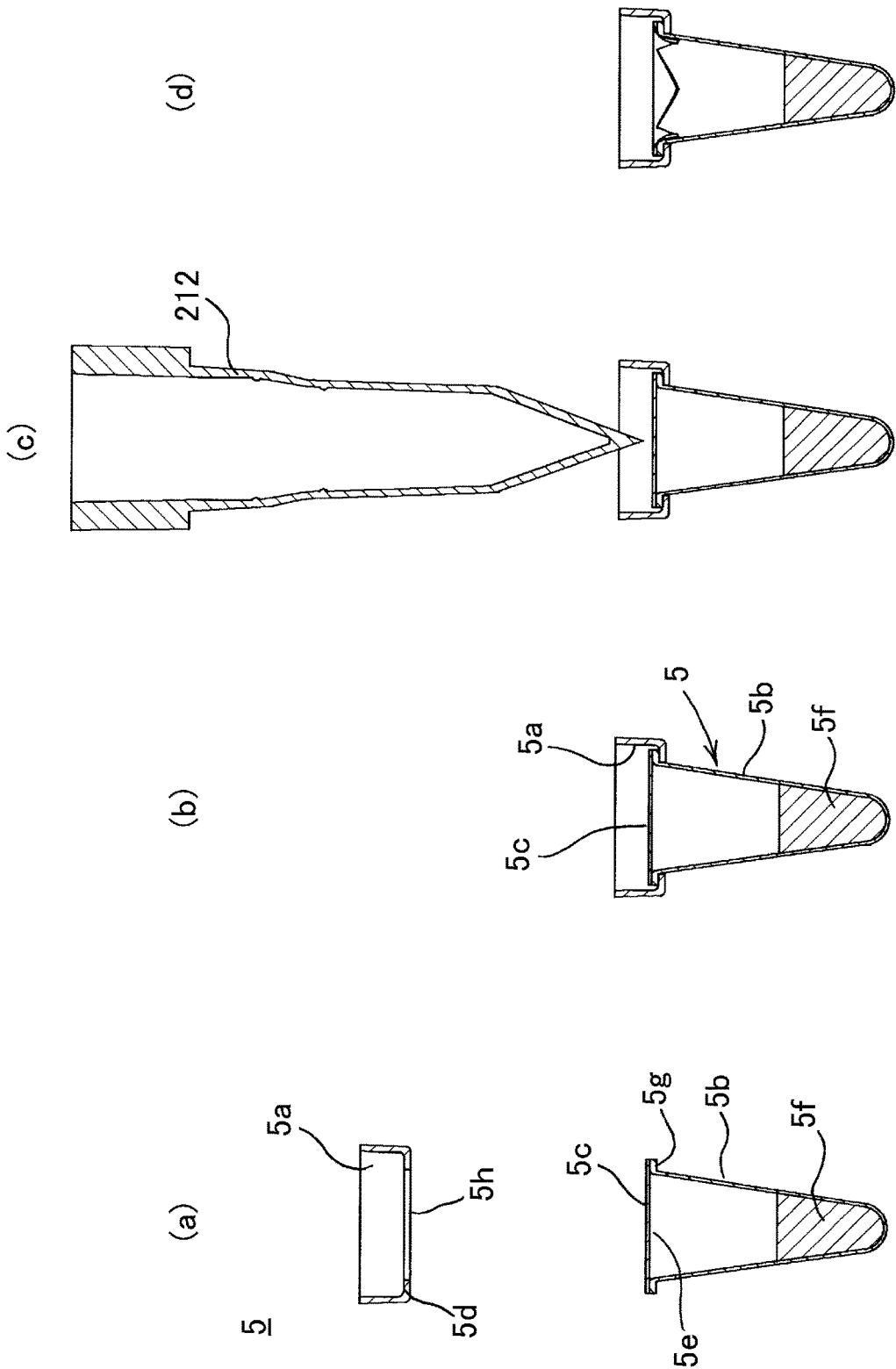
FIG. 7 is a housing part for reactions according to a third embodiment of the present invention, and a processing explanatory drawing thereof.

FIG. 7 is a housing part for reactions 5 according to a third embodiment of the present invention, and a processing explanatory drawing thereof.

As shown in FIG. 7(b), the housing part for reactions 5 according to the third embodiment has: a narrow-mouthed piping part 5b, whereby a solution for nucleic acid amplification or a portion thereof 5f, which represents the reaction reagent for nucleic acid amplification, is housed beforehand; a wide-mouthed piping part 5a that communicates with the narrow-mouthed piping part 5b, is provided on the upper side of the narrow-mouthed piping part 5b, and has a wider aperture than an aperture 5e of the narrow-mouthed piping part 5b; and a punchable film 5c formed from aluminum foil or the like, provided such that it partitions the interval between the wide-mouthed piping part 5a and the narrow-mouthed piping part 5b.

As shown disassembled in FIG. 7(a), the housing part for reactions 5 according to the third embodiment is different from the housing parts for reactions 1 and 3 according to the first and the second embodiment. In the housing part for reactions 5, the wide-mouthed piping part 5a and the narrow-mouthed piping part 5b are separately formed. A hole portion 5h is piercingly provided at the center of the bottom portion 5d of the wide-mouthed piping part 5a, and the narrow-mouthed piping part 5b has an aperture edge portion 5g along the outer circumference of its aperture 5e, that encloses the aperture 5e. The narrow-mouthed piping part 5b is provided such that, excluding the aperture edge portion 5g, it is able to pass through the hole portion 5h. The narrow-mouthed piping part 5b downwardly protrudes from the hole portion 5h of the wide-mouthed piping part 5a such that it passes through the hole portion 5h. The aperture edge portion 5g is mounted on the bottom portion 5d of the wide-mouthed piping part 5a, and the film 5c is attached to the aperture edge portion 5g of the narrow-mouthed piping part 5b. FIG. 7(c) is a drawing showing a state in which, in order to punch the film 5c of the reaction housing part 5 shown in FIG. 5(b) using the tip for punching 212 mounted on the nozzle head 50 mentioned below, it is positioned on the upper side thereof. FIG. 7(d) is a drawing showing a state in which, by lowering the tip for punching 212, the end is inserted into the narrow-mouthed piping part 5b, and the film 5c is punched.

In order to manufacture the housing part for reactions 5 according to the third embodiment, as shown in FIG. 7(a), in step 1, the wide-mouthed piping part 5a, in which the hole portion 5h is piercingly provided in the center of the bottom portion 5d, is manufactured by means of blow molding or injection molding using P.P or P.E for example, and the narrow-mouthed piping part 5b, which has the aperture edge portion 5g along the outer circumference of the aperture 5e that encloses the aperture 5e, is separately manufactured by blow molding using P.P. or P.E. for example.

In step 2, the reaction reagent or a portion thereof 5f is housed within the narrow-mouthed piping part 5b.

In step 3, an adhesive is applied on the upper side of the aperture edge portion 5g of the narrow-mouthed piping part 5b, and the aperture 5e is sealed by attaching the punchable film 5c using heat sealing or ultrasonic sealing such that there are no gaps, and the reaction reagent or a portion thereof 5f is enclosed within the narrow-mouthed piping part 5b. The film is composed of an aluminum layer and a resin layer.

In step 4, the narrow-mouthed piping part 5b, excluding its aperture edge portion 5g, downwardly protrudes such that it passes through the hole portion 5h of the wide-mouthed piping part 5a, and the housing part for reactions 5 is manufactured by mounting the lower side of the aperture edge portion 5g on the upper side of the bottom portion 5d of the wide-mouthed piping part 5a by applying an adhesive and attaching it by heat sealing or ultrasonic sealing such that there are no gaps. Here, a single-liquid moisture curing type multi-purpose elastic adhesive (HT-Bond Miracle 4 for example) is used as the adhesive for example.

Figure 8:
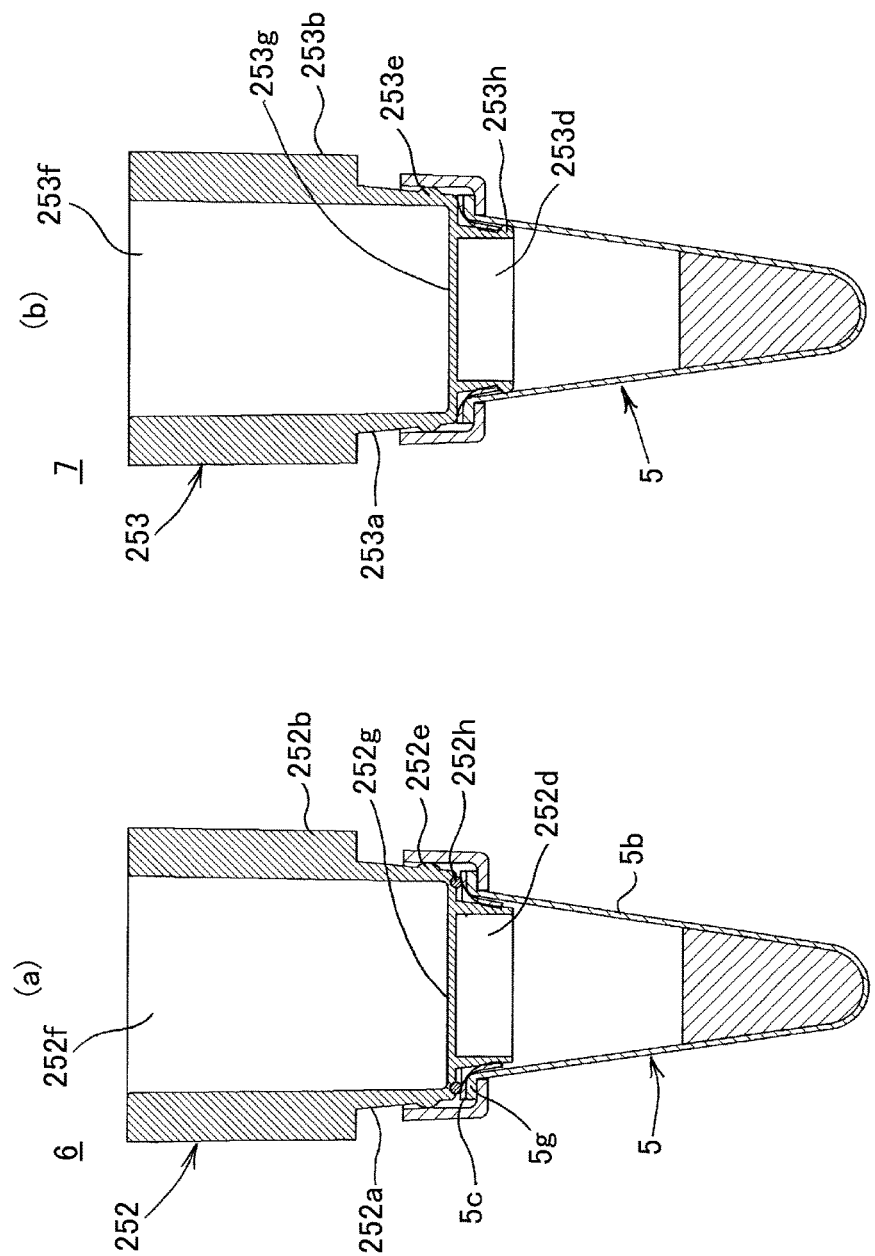
FIG. 8 is a drawing showing a sealing lid and a housing part for reactions according to a fourth embodiment of the present invention mounted with the same.

FIG. 8 is a drawing showing reaction containers 6 and 7 representing other examples using the housing part for reactions 5 according to the third embodiment.

FIG. 8(a) is a drawing showing a sealing lid 252, whereby an O ring 252h is provided along the edge of the lower side of the plug portion 252a such that it encloses the pushing portion 252d. Consequently, in a case where the sealing lid 252 is fitted to the wide-mouthed piping part 5a of the housing part for reactions 5 via the plug portion 252a, the interval between the film 5c attached to the aperture edge portion 5g of the narrow-mouthed piping part 5b and the sealing lid is sealed, and processing without fluid leakage can be performed.

FIG. 8B is a drawing showing a sealing lid 253, whereby a circular protrusion 253h is provided along the outer circumference of the end of the pushing portion 253d provided on the end of the plug portion 253a. Consequently, the film 5c, which is piercingly provided, is able to be pressed against the inner wall of the narrow-mouthed piping part 5b with certainty.

Figure 9:
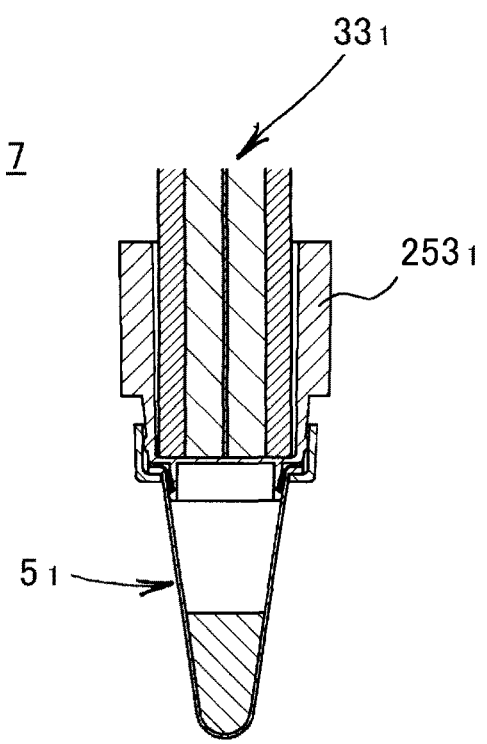
FIG. 9 is a drawing in which a linking portion is linked with the housing part for reactions according to the fourth embodiment of the present invention.

FIG. 9 is a drawing showing a state in which the sealing lid $253_i$ of the reaction container 7 shown in FIG. 8(b), and a linking portion 31i, are linked.

Figure 10:
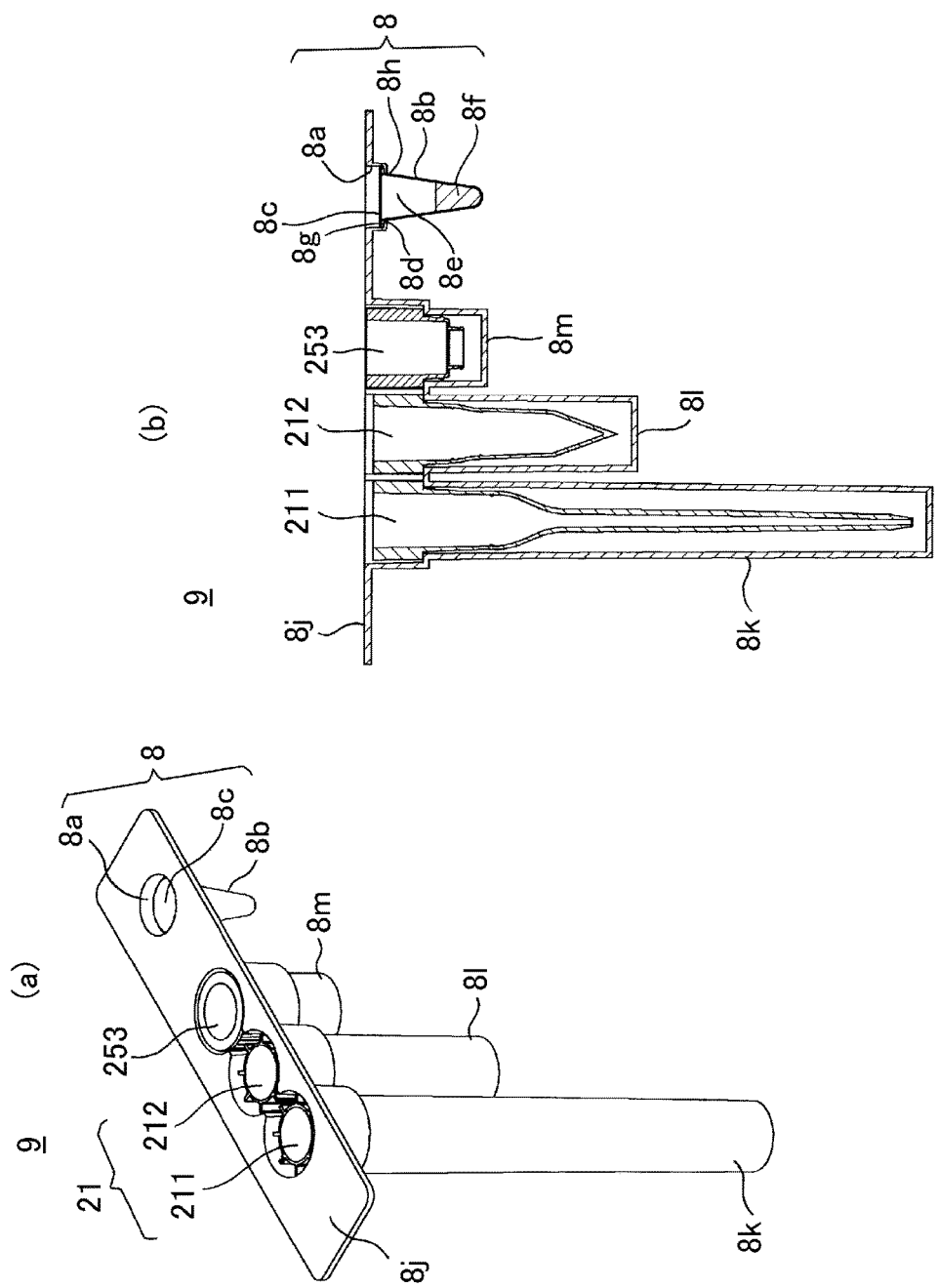
FIG. 10 is a drawing showing a cartridge container according to a fifth embodiment of the present invention.

FIG. 10 is a drawing showing a cartridge container 9 according to a fifth embodiment of the present invention, which further has a base plate 8j in which four concave portions (8, 8k, 8l and 8m) provided to the base plate 8j are arranged in a single row form. The housing part for reactions 8 is formed in the concave portion (8), the concave portion (8m) has a sealing lid housing part 8m that houses the sealing lid 253, the concave portion (8l) has a tip for punching housing part 8l that houses the tip for punching 212, and the concave portion (8k) has a dispensing tip housing part 8k that houses the dispensing tip 211.

In order to manufacture the cartridge container 9, in step s1, as shown in FIG. 10, the base plate 8j, in which the four concave portions 8a, 8k, 8l, and 8m are arranged in a single row form and the hole portion 8h is piercingly provided in the center of the bottom portion 8d of the concave portion (wide-mouthed piping part) 8a, is manufactured by means of blow molding or injection molding, and the like, using P.P. or P.E. for example, and the narrow-mouthed piping part 8b, which has the aperture edge portion 8g along the outer circumference of the aperture 8e that encloses the aperture 8e, is separately manufactured by blow molding using P.P. or P.E. for example.

In step s2, the reaction reagent or a portion thereof 8f is housed within the narrow-mouthed piping part 8b.

In step s3, an adhesive is applied on the upper side of the aperture edge portion 8g of the narrow-mouthed piping part 8b, and the aperture 8e is sealed by attaching the punchable film 8c using heat sealing or ultrasonic sealing for example, such that there are no gaps, and the reaction reagent or a portion thereof 8f is enclosed within the narrow-mouthed piping part 8b. The film is composed of an aluminum layer and a resin layer.

In step s4, the narrow-mouthed piping part 8b, excluding the aperture edge portion 8g thereof, downwardly protrudes such that it passes through the hole portion 8h of the wide-mouthed piping part 5a, and the housing part for reactions 8 is manufactured by mounting the lower side of the aperture edge portion 8g on the upper side of the bottom portion 8d of the wide-mouthed piping part 8a by applying an adhesive and attaching it using heat sealing or ultrasonic sealing such that there are no gaps. Here, a single-liquid moisture curing type multi-purpose elastic adhesive (HT-Bond Miracle 4 for example) is used as the adhesive for example.

In step s5, the cartridge container 9 is manufactured by means of the dispensing tip 211, the tip for punching 212, and the sealing lid 253 being housed in the respective concave portions 8k, 8l, and 8m.

Figure 11:
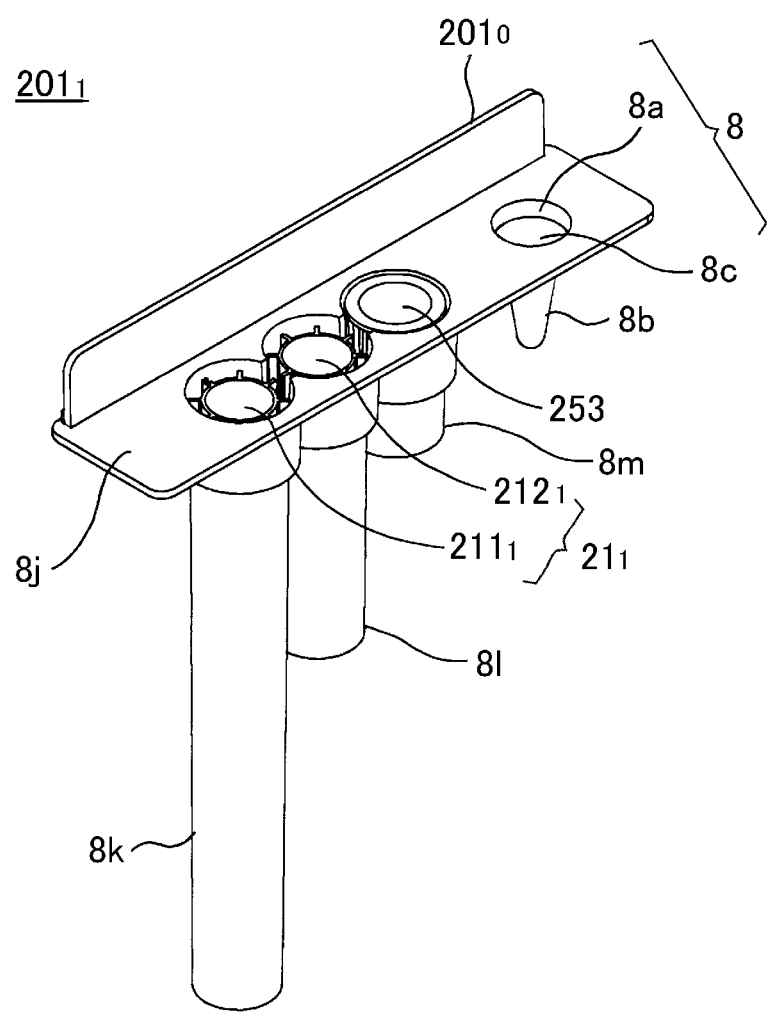
FIG. 11 is a drawing showing a cartridge container according to a sixth embodiment of the present invention.

FIG. 11 is a drawing showing a cartridge container $201_1$ according to a sixth embodiment of the present invention, wherein a partition wall $201_0$ is provided to the cartridge container 9 shown in FIG. 10 along the row direction (the movement path of the nozzles) in which the concave portions are arranged. This is represented by reference symbol $201_1$. Hereunder, a reaction container light measurement device 10 which represents a reaction container system utilizing the cartridge container $201_1$ is described.

Figure 12:
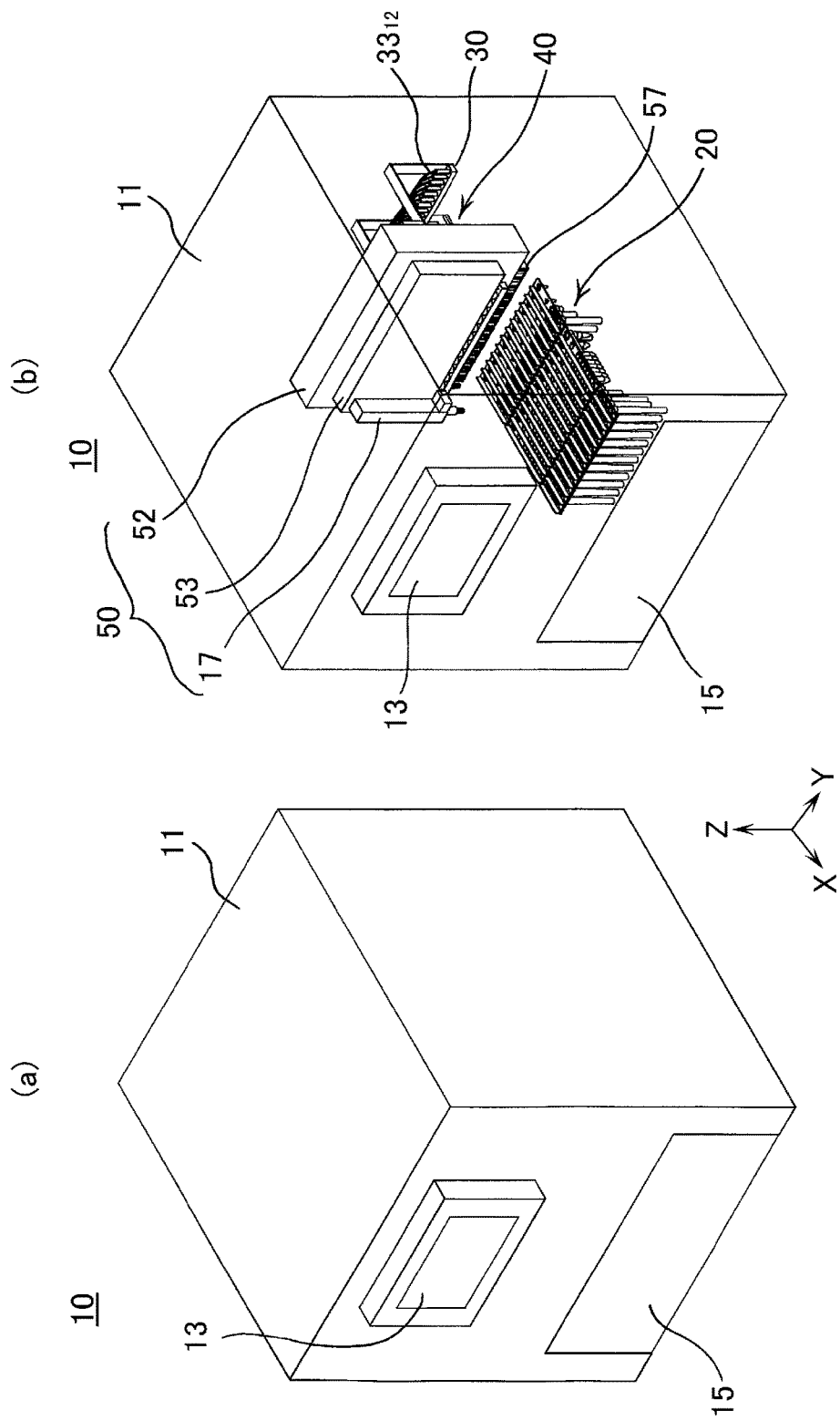
FIG. 12 is an overall perspective view showing a reaction container system according to a seventh embodiment of the present invention.

Hereunder, the reaction container light measurement device 10 mentioned above which represents a reaction container system according to a seventh embodiment of the present invention, is described more specifically with reference to FIG. 12 to FIG. 18. FIG. 12 is a see-through perspective view showing an external view of the reaction container light measurement device 10.

FIG. 12(a) is a drawing showing an external view of the reaction container light measurement device 10, which has: an enclosure 11 with a size of 500 mm in depth (Y axis direction), 600 mm in width (X axis direction), and 600 mm in height (Z axis direction) for example, in which the container group 20, the nozzle head 50, a nozzle head transfer mechanism, and a CPU+program are housed in the interior; a control panel 13 provided on the enclosure 11; and a drawer 15 to which a stage is provided.

FIG. 12(b) is a perspective view that sees through the interior of the enclosure 11, wherein the stage, into which container group 20 is built-in, is able to be drawn out to the exterior by means of the drawer 15, and further, the nozzle head 50 is movably provided in the X axis direction with respect to the container group 20 by means of the nozzle head transfer mechanism.

FIG. 12(b) is a drawing showing that the nozzle head 50 is largely provided with: various transfer mechanisms 52 having an arranging body Y axis transfer mechanism 41, a stage Z axis transfer mechanism 35, and a nozzle Z axis transfer mechanism 75; a traversable nozzle suction-discharge mechanism 17; the measuring device 40; a connecting end arranging body 30; an optical fiber (bundle) $33_i$; and the magnetic force part 57. The traversable nozzle suction-discharge mechanism 17 and the traversable nozzles $71_0$ are supported such that they are movable in the Y axis direction by means of the arranging body Y axis transfer mechanism 41 such that they traverse the exclusive regions $20_i$.

Figure 13:
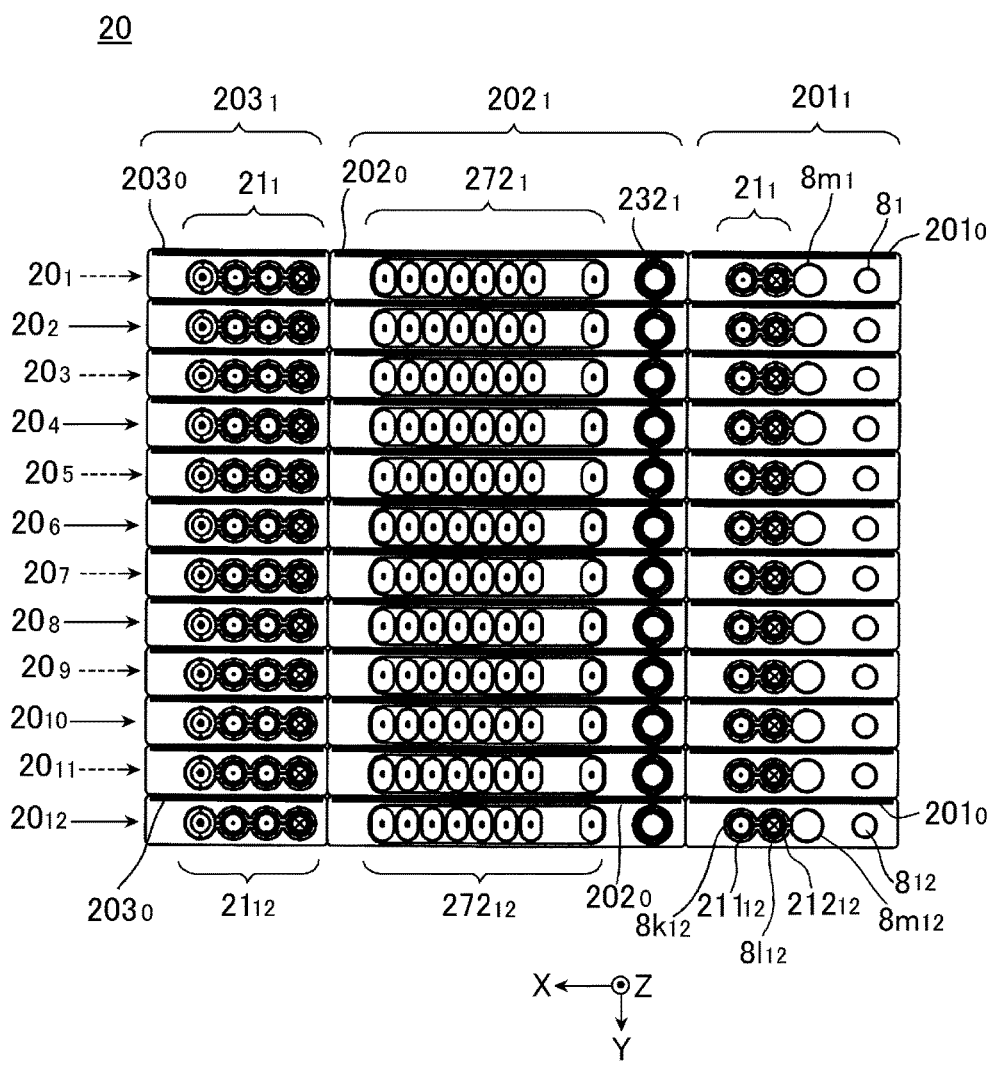
FIG. 13 is a plan view showing enlarged, a container group of the reaction container system shown in FIG. 12.

FIG. 13 is a plan view showing enlarged, the container group 20 shown in FIG. 12. The container group 20 is one in which twelve exclusive regions $20i$ (i=1, . . . 12), wherein the longitudinal direction thereof is along the X axis direction and housing parts are arranged in a single row form, are arranged in parallel along the Y axis direction at a pitch of 18 mm for example. The exclusive regions $20_i$ are separately provided with a cartridge container for PCR amplification $201_i$, a cartridge container for nucleic acid extraction $202_i$, and a cartridge container for housing tips $203_i$ according to the sixth embodiment of the present invention. The prevention of cross-contaminations between the exclusive regions $20_i$ is achieved by providing partition walls $201_0$, $202_0$, and $203_0$ on the cartridge containers $201_i$, $202_i$, and $203_i$ of the exclusive regions $20_i$ on the edge of one side along the X axis direction.

The cartridge container for PCR amplification $201_1$ has: the housing part for reactions $8_i$ that, in addition to being detachably linked with the twelve linking portions $31_i$ provided to the light guide stage 32 via a single sealing lid $253_i$ which has transparency, houses beforehand the solutions for nucleic acid amplification such as a buffer solution necessary for the PCR reaction; sealing lid housing parts $25_i$ housing the sealing lids $253_i$; tips for punching $212_i$ for punching the punchable film 8c covering the housing parts for reactions $8_i$ and the narrow-mouthed piping parts $8b_i$; and housing parts for tips and the like $21_i$ that respectively house the dispensing tips $211_i$. It is preferable to provide a barcode that displays the sample information and the inspection information relating to the cartridge container for PCR amplification $201_i$.

The cartridge container for nucleic acid extraction $202_i$ has: seven liquid housing parts $272_i$ for example, that house various reagents for nucleic acid extraction; tubes for reactions Y $232_i$ that house the extracted nucleic acids; and barcodes $82_i$ that display various information, such as the sample information and the inspection information, related to the cartridge container. The housing parts for reactions $8_i$ and the tubes for reactions $232_i$ are temperature controllable by means of the temperature controller 29.

The cartridge container for housing tips $203_i$ has: a tip for punching that is able to punch the film covering the cartridge container for nucleic acid extraction $202_i$; two small-quantity dispensing tips that perform the dispensing of small quantities of liquids; and housing parts for tips and the like $21_i$ that house dispensing tips for separations that are able to perform separation by adsorbing magnetic particles on an inner wall by applying and removing a magnetic force from the exterior. It is preferable to provide a barcode that display various information relating to the cartridge container $203_i$.

The capacity of the housing part for reactions $8_i$ is of the order of approximately 200 µL, and the capacity of the other reaction containers, liquid housing parts, and tubes is of the order of approximately 2 mL.

The housing part for reactions $8_i$ is used for the amplification of nucleic acids or the fragments thereof, and temperature control is performed by means of the temperature controller 29 based on a predetermined amplification method, such as a thermal cycle (from 4° C. to 95° C.) for example. The housing part for reactions $8_i$ is formed with two levels as shown in FIG. 10(b) for example, and has a narrow-mouthed piping part $8b_i$ provided on the lower side in which the solution for amplification $8f_i$ is housed, and a wide-mouthed piping part $8a_i$ provided on the upper side in which the sealing lid $253_i$ is fittable. The inner diameter of the wide-mouthed piping part $8a_i$ is 8 mm for example, and the inner diameter of the aperture of the narrow-mouthed piping part $8b_i$ is approximately 5 mm for example. The tubes for reactions $232_i$ housed in the reaction tube housing holes are temperature controlled for incubation to a constant temperature of 55° C. for example.

The liquid housing part group $272_i$ houses the solutions for separating and extracting as follows. A first liquid housing part houses 40 µL of Lysis 1, a second liquid housing part houses 200 µL of Lysis 2, a third liquid housing part houses 500 µL of a binding buffer solution, a fourth liquid housing part houses a magnetic particle suspension, a fifth liquid housing part houses 700 µL of the washing liquid 1, a sixth liquid housing part houses 700 µL of the washing liquid 2, a seventh liquid housing part houses 50 µL of distilled water as a dissociation liquid, and an eighth liquid housing part, which is slightly separated, houses 1300 µL of isopropyl alcohol (isopropanol) used for the removal of protein and the like, as a portion of the solution for separating and extracting protein. The respective reagents and the like are prepacked as a result of the punchable film covering the respective apertures thereof.

In addition, 1.2 mL of distilled water is housed in a separate distilled water reservoir, and tubes that house suspensions of bacteria, cells, and the like, or samples such as whole blood, are separately prepared for each of the respective exclusive regions $20_i$.

Figure 14:
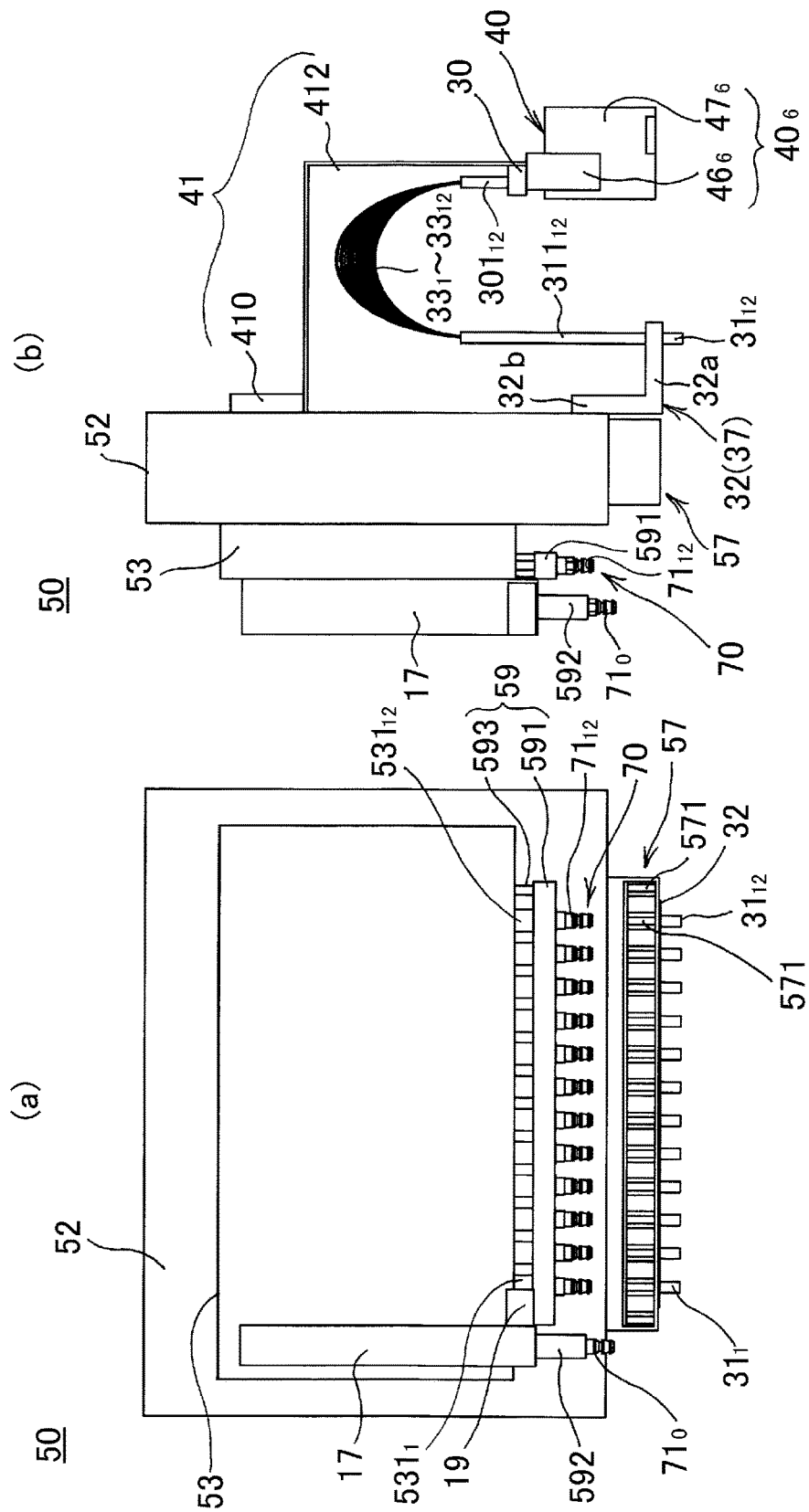
FIG. 14 is a plan view showing enlarged, the whole nozzle head of the reaction container system shown in FIG. 12.
Figure 15:
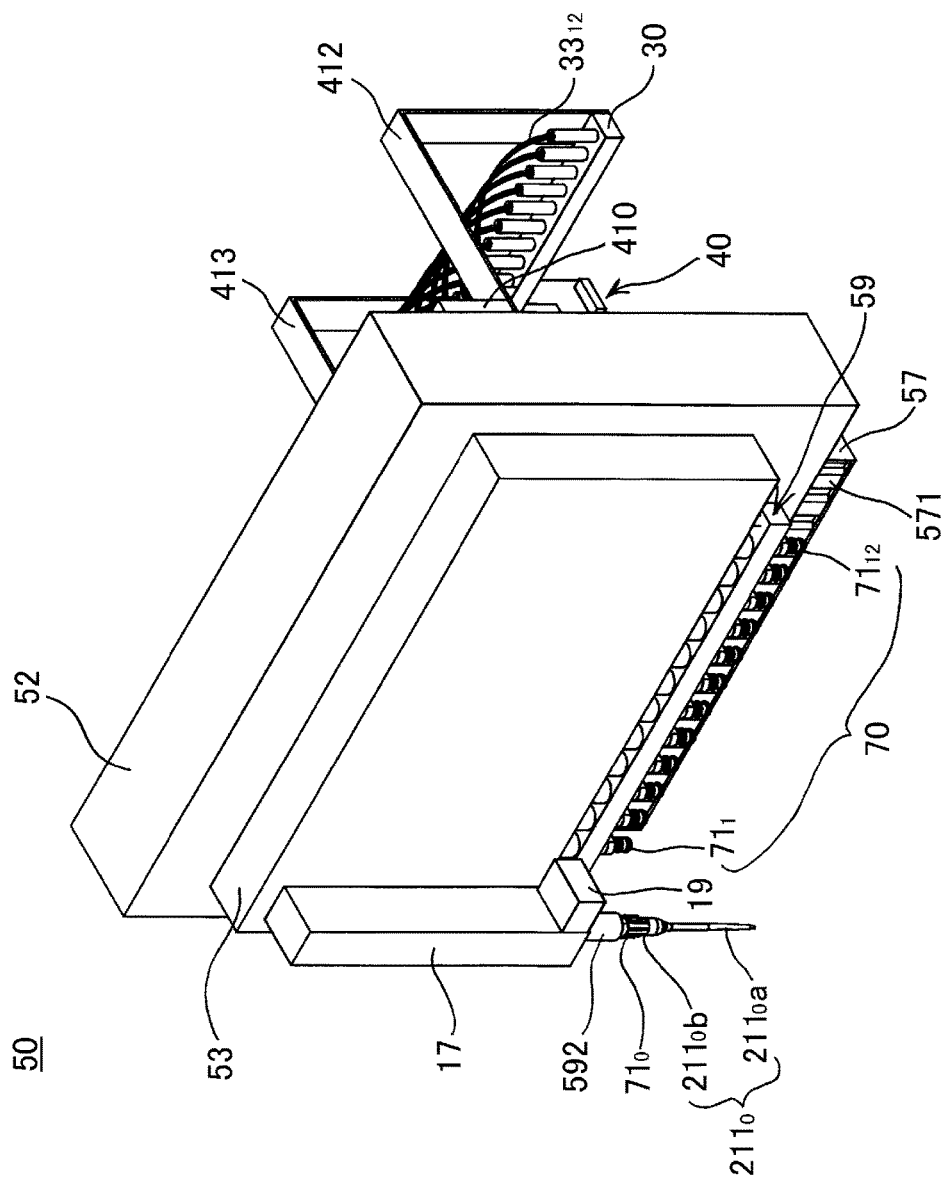
FIG. 15 is a front side perspective view of the nozzle head of the reaction container system shown in FIG. 14.

FIG. 14 is a front view and a side view of the nozzle head 50 according to the seventh embodiment of the present invention, and FIG. 15 is a perspective view from the front side.

The nozzle head 50 is one having: a nozzle arranging portion 70 in which twelve nozzles $71_i$ are arranged; a tip detaching mechanism 59 that is able to detach dispensing tips $211_i$ mounted on the nozzles $71_i$; a suction-discharge mechanism 53; a magnetic force part 57 having twelve magnets 571 provided such that they are able to approach and separate with respect to the dispensing tips $211_i$; a light guide stage 32; twelve linking portions $31_i$ provided to the light guide stage 32; a transfer mechanism portion 52 having a nozzle Z axis transfer mechanism 75 and a stage Z axis transfer mechanism 35; optical fibers (bundles) $33_i$ representing flexible light guide portions that extend to the rear side from the linking portions $31_i$; a connecting end arranging body 30; the arranging body Y axis transfer mechanism 41; a measuring device 40 having a measuring end 44; a traversable nozzle $71_0$; and a suction-discharge mechanism 17 thereof.

The nozzle arranging portion 70 is provided with a cylinder supporting member 73 that supports twelve cylinders $531_i$ such that they are arranged along the Y axis direction at the predetermined pitch of 18 mm for example. The nozzles $71_i$ are provided on the downward end of the cylinders $531_i$ such that they are communicated with the cylinders $531_i$.

The tip detaching mechanism 59 is provided with detaching shafts 593 on both sides, and has a tip detaching member 591 that detaches the twelve dispensing tips $211_i$ from the nozzles $71_i$ by sliding in the vertical direction.

Figure 16:
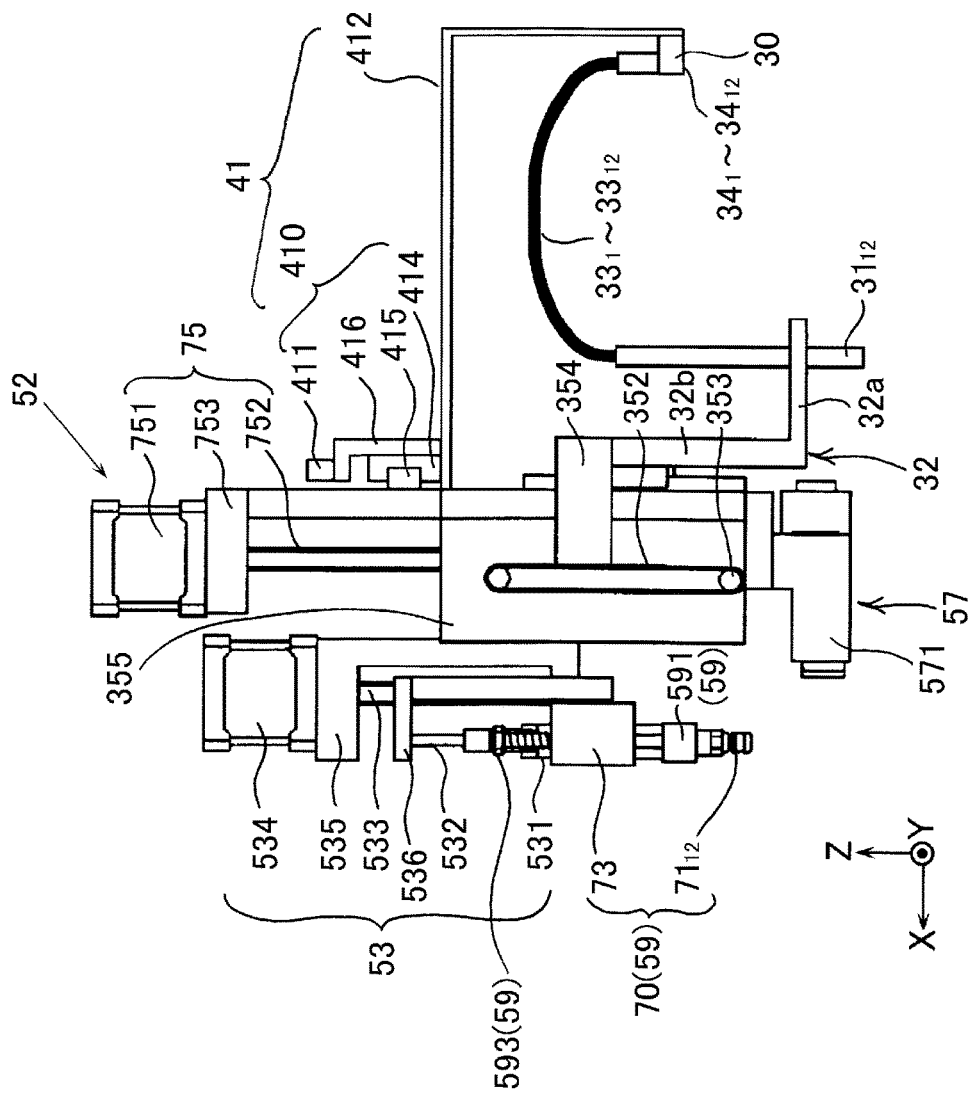
FIG. 16 is a perspective view showing more specifically the transfer mechanism and the suction-discharge mechanism shown in FIG. 14.
Figure 17:
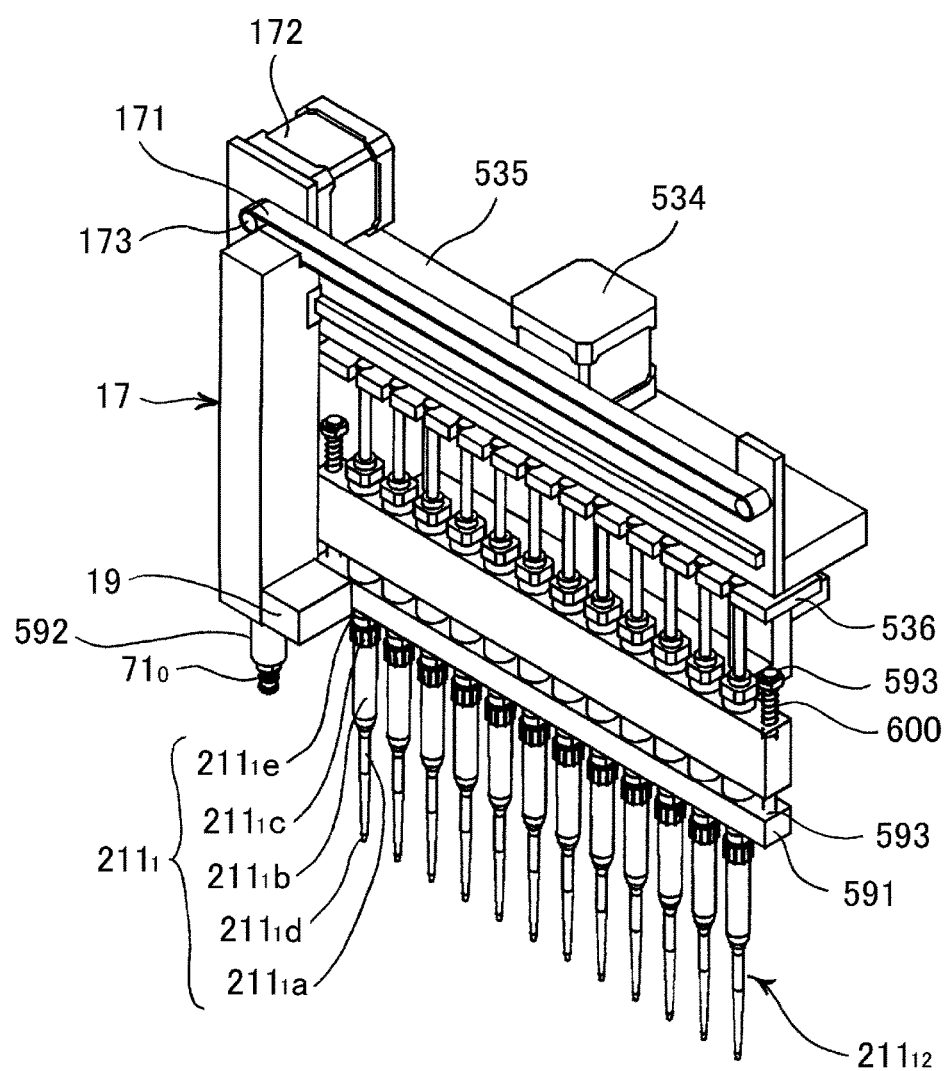
FIG. 17 is a perspective view showing more specifically the suction-discharge mechanism shown in FIG. 14.

As shown specifically in FIG. 16 and FIG. 17, the tip detaching member 591 is interlocked with the lowering of two tip detaching shafts 593 and detaches the dispensing tips $211_i$ from the nozzles $71_i$. The tip detaching shaft 593 is elastically supported by the cylinder support member 73 by means of a spring 600 wrapped around the outer periphery such that it is biased in the upward direction, and the upper end thereof is positioned above the upper ends of the cylinders $531_i$ but below the lower limit position of the vertical movement range of the normal suction and discharge of a cylinder drive plate 536 mentioned below. The two tip detaching shafts 593 are pushed in the downward direction by means of the cylinder drive plate 536 exceeding the vertical movement range and being lowered near the upper end of the cylinder $531_i$, thus lowering the tip detaching member 591. The tip detaching member 591 has twelve holes having an inner diameter that is larger than the outer diameter of the nozzles $71_i$ but smaller than the mounting portions $211_ic$, which represents the largest outer diameter of the dispensing tips $211_i$, arranged at the pitch mentioned above such that the nozzles $71_i$ pass therethrough.

As shown specifically in FIG. 16 and FIG. 17, the suction-discharge mechanism 53 has: the cylinders $531_i$ for performing suction and discharge of gases with respect to the dispensing tips $211_i$ which are communicated with the nozzles $71_i$ and mounted on the nozzles $71_i$, and a piston rod 532 that slides within the cylinders $531_i$; a drive plate 536 that drives the piston rod 532; a ball screw 533 that threads with the drive plate 536; a nozzle Z axis movable body 535 that, in addition to axially supporting the ball screw 533, is integrally formed with the cylinder support member 73; and a motor 534 mounted on the nozzle Z axis movable body 535 that rotatingly drives the ball screw 533.

The magnetic force part 57 has a magnet 571 that is provided such that it can approach and separate with respect to the narrow diameter portions $211_ia$ of the dispensing tips $211_i$ detachably mounted on the nozzles $71_i$, and is able to apply and remove a magnetic field in the interior of the dispensing tips $211_i$.

As shown specifically in FIG. 16, the nozzle Z axis transfer mechanism 75 has: a ball screw 752 that threads with the Z axis movable body 535 and vertically moves the Z axis movable body 535 along the Z direction; a nozzle head substrate 753 that axially supports the ball screw 752, and in addition to axially supporting the magnet 571 on the lower side thereof such that it is movable in the X axis direction, is itself movable in the X axis direction by means of the nozzle head transfer mechanism 51 mentioned below; and a motor 751 provided on the upper side of the nozzle head substrate 753 that rotatingly drives the ball screw 752.

As shown specifically in FIG. 16, the light guide stage 32 comprises a horizontal plate 32a and a vertical plate 32b, which are letter-L shaped plates in cross-section, and is provided with twelve cylinder-shaped linking portions $31_i$ having ends of optical fibers (bundles) $33_i$, which are directly or indirectly linkable with the apertures of the PCR tubes $231_i$ and are optically connected with the interior of the linked PCR tubes $231_i$, protruding in the downward direction from the horizontal plate 32a. Furthermore, a heater 37 that heats the sealing lids $251_i$ mounted on the linking portions $31_i$ and prevents condensation, is built into the bases of the linking portions $31_i$. The temperature of the heater is set to approximately 105° C. for example. Since the light guide stage 32 is supported by the nozzle head substrate 753 by means of the nozzle head stage Z axis transfer mechanism 35 such that it is movable in the Z axis direction, it is movable in the nozzle X axis direction and Z axis direction.

The stage Z axis transfer mechanism 35 has: a side plate 355 provided on the nozzle head substrate 753; a mount driving band-shaped member 354 that is supported by a timing belt 352 spanning between two sprockets 353 arranged in the vertical direction axially supported by the side plate 355, and vertically moves in the Z axis direction; and a motor attached to the rear side of the nozzle head substrate 753 that rotatingly drives the sprockets 353.

As shown in FIG. 17, the traversable nozzle suction-discharge mechanism 17 is provided with a tip detaching mechanism 592 on the lower side of the suction-discharge mechanism 17 and on the upper side of the nozzle $71_0$. Furthermore, the suction-discharge mechanism 17 is provided with a digital camera 19. The suction-discharge mechanism 17 is movably provided in the Y axis direction by being attached to a timing belt 171 spanning between two sprockets 173 that are rotatingly driven by a motor 172.

Figure 18:
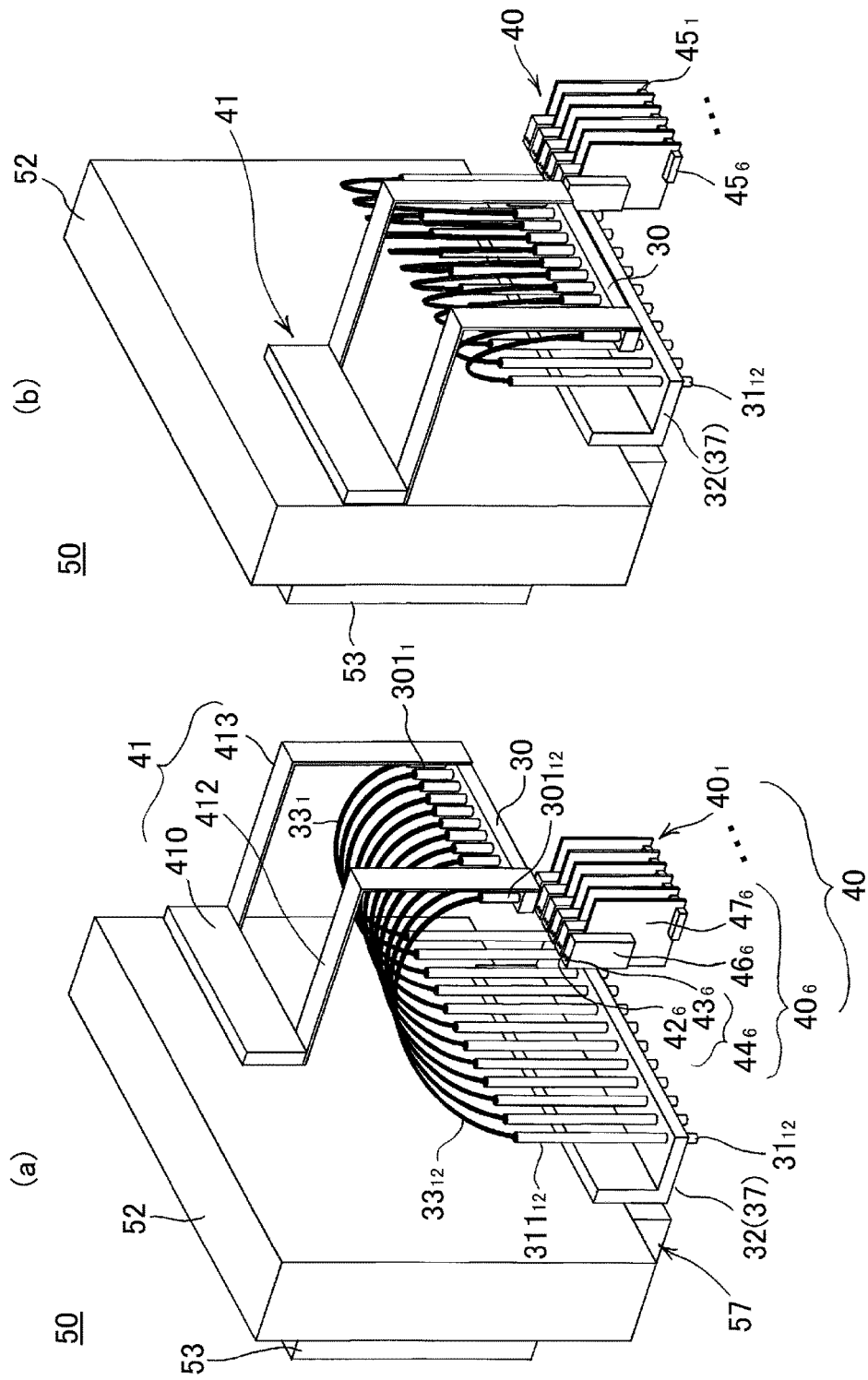
FIG. 18 is a perspective view of the nozzle head shown in FIG. 14 viewed from the rear side.

FIG. 18 represents two perspective views of the nozzle head according to the seventh embodiment viewed from the rear side, which show the connection starting position (FIG. 18(a)) and the connection finishing position (FIG. 18(b)) at the time the respective connecting ends of the connecting end arranging body 30 and the respective measuring ends are successively optically connected.

The linking portions $31_i$ are provided with the ends of the optical fibers (bundles) $33_i$, and have: a connecting end arranging body 30 in which the connecting ends $34_i$ which pass through the horizontal plate 32a of the light guide stage 32, and the rear ends thereof provided corresponding to the respective linking portions $31_i$, are arranged on an arranging surface on a path along a straight line in the Y axis direction, which represents a predetermined path, at a shorter spacing than the spacing of the linking portions $31_i$; and six measuring ends that are provided in the vicinity of, or making contact with, the arranging surface, and are successively optically connectable with the connecting ends $34_i$ along the straight line. There is also provided a measuring device 40 in which, by means of optical connections between the connecting ends and the measuring ends, the fluorescent light within the housing parts for reactions $8_i$, which represents the optical state, is receivable, and excitation light is also able to be irradiated.

Furthermore, the light guide stage 32 has a cylinder-shaped body $311_i$, which retains the optical fibers (bundles) $33_i$ extending to the rear side from the linking portions $31_i$ such that they pass through the interior in order to prevent folding, protrudingly provided upward from the horizontal plate 32a directly above the linking portions $31_i$. In the same manner, the connecting end arranging body 30 is also provided with a cylinder-shaped body $301_i$, which retains the optical fibers (bundles) $33_i$ extending from the connecting ends $34_i$ such that they pass through the interior in order to prevent folding, on the connecting end $34_i$ side.

The arranging body Y axis transfer mechanism 41 that moves the connecting end arranging body 30 in the Y axis direction has: arms 412 and 413 provided to the connecting end arranging body 30; a joining body 411 that joins the arms 412 and 413 and the timing belt; a guide rail 414 that guides the Y axis movement of the joining body 411; and two sprockets spanned by the timing belt and arranged along the Y axis direction.

The measuring device 40 is one that supports the measurement of fluorescent light and comprises six types of specific wavelength measuring devices $40_j$ that are linearly aligned along a straight line in the Y axis direction, which represents the predetermined path, such that they support the measurement of six types of fluorescent light, and they are provided fixed on a substrate of the nozzle head 50, such as the frame that encloses the transfer mechanism portion 52, or a member that supports the same. Therefore, depending on the mechanism provided to the transfer mechanism portion 52, the measuring device 40 does not move.

The measuring device 40 is one in which the measuring ends of the plurality of types (six in this example) of specific wavelength measuring devices $40_j$ (j=1, 2, 3, 4, 5, 6), and therefore, in this case, the specific wavelength measuring devices $40_j$ themselves are aligned in a single row form, and integrally fixed to a member joined with the nozzle head substrate 753 using fixtures $45_j$. The specific wavelength measuring devices $40_j$ have: measuring ends $44_j$ arranged along a straight line path in the Y axis direction which represents the predetermined path, such that they successively optically connect to the connecting ends $34_i$; light detectors $46_j$ in which an optical system having an irradiation source that irradiates excitation light to the PCR tubes $231_i$ and a light receiving portion that receives the fluorescent light generated in the housing part for reactions $8_i$ are built-in; and circuit boards $47_j$. The measuring ends $44_j$ have first measuring ends $42_j$ that optically connect with the irradiation source, and second measuring ends $43_j$ that optically connect with the light receiving portion. Here, the light detectors $46_j$ and the circuit boards $47_j$ correspond to the measuring device main body.

The pitch between the respective connecting ends $34_i$, assuming a pitch between the linking portions $31_i$ of 18 mm, is 9 mm, which is half thereof. Then, the pitch between the measuring ends $44_j$ is 9 mm or less for example.

There is a case where the first measuring ends $42_j$ and the second measuring ends $43_j$ of the measuring ends $44_j$ of the respective specific wavelength measuring devices $40_j$ are arranged aligned in a lateral direction (Y axis direction) along the straight line of the Y axis direction along the predetermined path, and a case where they are arranged aligned in a longitudinal direction (X axis direction). In the former case, without stopping the emission of the excitation light, the respective measuring devices successively receive light at a timing for receiving light determined based on the speed of the connecting end arranging body, the pitch between the connecting ends, the distance between the first measuring ends and the second measuring ends of the measuring ends, and the pitch between the measuring ends.

On the other hand, in the latter case, as shown in FIG. 18, with respect to the connecting end, a first connecting end and a second connecting end are provided. The first connecting end connects only with the first measuring ends $42_j$, and the second measuring ends $43_j$ connect only with the second connecting end. The fixed path represents two paths. Furthermore, the optical fibers (bundles) $33_i$ have optical fibers (bundles) $331_i$ for receiving light that have the first connecting end, and optical fibers (bundles) $332_i$ for irradiation that have the second connecting end. In this case, compared to the former case, connection with the linking portions is performed by means of optical fibers in which the irradiation source and the light receiving portion are dedicated, and therefore, the control is simple, and the reliability is high since optical fibers that are respectively suitable for irradiation and receiving light can be used.

The speed of the connecting end arranging body 30 with respect to the measuring ends $44_j$ is determined with consideration of the stable light receivable time, the lifetime of the fluorescent light with respect to excitation light irradiation, the number of connecting ends, the pitch between the connecting ends, and the like (the distance of the predetermined path). In the case of a real-time PCR measurement, it is controlled such that it becomes 100 mm to 500 mm per second for example. In the present embodiment, since the movement is performed by sliding the arranging surface with respect to the measuring ends 44, the incidence of optical noise to the measuring ends 44 can be prevented. Furthermore, the connecting end arranging body 30 moves with respect to the measuring ends intermittently such that it momentarily stops at each pitch advance between the connecting ends or between the measuring ends, or continuously.

Next, a series of processing operations that perform real-time PCR of the nucleic acids of a sample containing bacteria using the reaction container light measurement device 10 according to the seventh embodiment is described. Step S1 to step S13 below correspond to separation and extraction processing.

In step S1, the drawer 15 of the reaction container light measurement device 10 shown in FIG. 12 is opened, the container group 20 is pulled out, and by utilizing a feeding device for samples and the like, which is provided separately from the container group 20, the samples which are subject to testing, various washing liquids, and various reagents, are supplied beforehand, and furthermore, a liquid housing part in which reagents and the like are prepacked is mounted.

In step S2, following returning of the container group 20 and closing of the drawer 15, the start of the separation and extraction and amplification processing is instructed by means of the operation of the touch panel of the control panel 13 for example.

In step S3, the extraction control part provided to the nucleic acid processing controller of the CPU+program of the reaction container light measurement device 10 instructs the nozzle head transfer mechanism 51 and moves the nozzle head 50 in the X axis direction, positions the tip for punching mounted to the nozzle $71_i$ above the first liquid housing part of the liquid housing part group $27_i$ of the container group, and punches the film covering the aperture of the liquid housing part by lowering the nozzle by means of the nozzle Z axis transfer mechanism 75, and in the same manner, the other liquid housing parts of the liquid housing part group $27_i$ and the reaction container group $23_i$ are successively punched by moving the nozzle head 50 in the X axis direction.

In step S4, the nozzle head 50 is again moved in the X axis direction and moved to the housing part for tips and the like $21_i$, and the nozzles $71_i$ are lowered by means of the nozzle Z axis transfer mechanism 75, and the dispensing tips $211_i$ are mounted. Next, after being raised by the nozzle Z axis transfer mechanism 75, the dispensing tips $211_i$ are moved along the X axis by means of the nozzle head transfer mechanism 51, and advanced to the eighth liquid housing part of the liquid housing part group $27_i$. Then a predetermined amount of isopropanol is aspirated from the liquid housing part, and they are again moved along the X axis direction, and predetermined amounts are respectively dispensed into the solution components (NaCl, SDS solutions) housed in the third liquid housing part and the fifth liquid housing part, and the distilled water housed in the sixth liquid housing part, so that 500 μL of a binding buffer solution (NaCl, SDS, isopropanol), 700 μL of a washing liquid 1 (NaCl, SDS, isopropanol), and 700 μL of a washing liquid 2 (water 50%, isopropanol 50%) are respectively prepared as solutions for separating and extracting within the third, the fifth, and the sixth liquid housing parts.

In step S5, following movement to, among the housing parts for tips and the like $21_i$, the sample tube in which the sample is separately housed, the narrow diameter portion $211_i a$ of the dispensing tip $211_i$ is loweringly inserted using the nozzle Z axis transfer mechanism 75, and, with respect to the suspension of the sample housed in the sample tube, following suspension of the sample within the liquid by repeating the suction and the discharge by raising and lowering the drive plate 536 of the suction-discharge mechanism 53, the sample suspension is aspirated within the dispensing tip $211_i$. The sample suspension is moved along the X axis by means of the nozzle head transfer mechanism 51 to the first liquid housing part of the liquid housing part group $27_i$ housing the Lysis 1 (enzyme) representing the solution for separating and extracting, and the narrow diameter portion $211_ia$ of the dispensing tip $211_i$ is inserted through the hole in the punched film, and the suction and the discharge is repeated in order to stir the sample suspension and the Lysis 1.

In step S6, the entire amount of the stirred liquid is aspirated by the dispensing tip $211_i$, and incubation is performed by housing it in the reaction tube retained in the storage cavity $232_i$ that is set to 55° C. by means of the constant temperature controller. Consequently, the protein contained in the sample is broken down and made a low molecular weight. After a predetermined time has elapsed, the reaction mixture is left in the reaction tube, the dispensing tip $211_i$ is moved to the second liquid housing part of the liquid housing part group $27_i$ by means of the nozzle head transfer mechanism 51, and the entire amount of the liquid housed within the second liquid housing part is aspirated by using the nozzle Z axis transfer mechanism 75 and the suction-discharge mechanism 53, and it is transferred using the dispensing tip $211_i$ by means of the nozzle head transfer mechanism 51, and the reaction solution is discharged within the third liquid housing part by penetrating the hole in the film and inserting the narrow diameter portion.

In step S7, the binding buffer solution housed within the third liquid housing part, which represents a separation and extraction solution, and the reaction solution are stirred, the solubilized protein is further dehydrated, and the nucleic acids or the fragments thereof are dispersed within the solution.

In step S8, using the dispensing tip $211_i$, the narrow diameter portion thereof is inserted into the third liquid housing part by passing through the hole in the film, the entire amount is aspirated and the dispensing tip $211_i$ is raised by means of the nozzle Z axis transfer mechanism 75, and the reaction solution is transferred to the fourth liquid housing part, and the magnetic particle suspension housed within the fourth liquid housing part is stirred with the reaction solution. A cation structure in which Na+ ions bind to the hydroxyl groups formed on the surface of the magnetic particles contained within the magnetic particle suspension is formed. Consequently, the negatively charged DNA is captured by the magnetic particles.

In step S9, the magnetic particles are adsorbed on the inner wall of the narrow diameter portion $211_ia$ of the dispensing tip $211_i$ by approaching the magnet 571 of the magnetic force part 57 to the narrow diameter portion $211_ia$ of the dispensing tip $211_i$. In a state in which the magnetic particles are adsorbed on the inner wall of the narrow diameter portion $211_ia$ of the dispensing tip $211_i$, the dispensing tip $211_i$ is raised by means of the nozzle Z axis transfer mechanism 75 and moved from the fourth liquid housing part to the fifth liquid housing part using the nozzle head transfer mechanism 51, and the narrow diameter portion $211_ia$ is inserted by passing through the hole in the film.

In a state in which the magnetic force within the narrow diameter portion $211_ia$ is removed by separating the magnet 571 of the magnetic force part 57 from the narrow diameter portion $211_ia$ of the dispensing tip $211_i$, by repeating the suction and the discharge of the washing liquid 1 (NaCl, SDS, isopropanol) housed in the fifth liquid housing part, the magnetic particles are released from the inner wall, and the protein is washed by stirring within the washing liquid 1. Thereafter, in a state in which the magnetic particles are adsorbed on the inner wall of the narrow diameter portion $211_ia$ as a result of approaching the magnet 571 of the magnetic force part 57 to the narrow diameter portion $211_ia$ of the narrow diameter portion $211_ia$ again, the dispensing tip $211_i$ is, by means of the nozzle Z axis transfer mechanism 75, moved from the fifth liquid housing part to the sixth liquid housing part by means of the nozzle head transfer mechanism 51.

In step S10, the narrow diameter portion $211_ia$ of the dispensing tip $211_i$ is inserted by passing through the hole in the film using the nozzle Z axis transfer mechanism 75. By repeating the suction and the discharge of the washing liquid 2 (isopropanol) housed in the sixth liquid housing part in a state in which the magnetic force within the narrow diameter portion $211_ia$ is removed by separating the magnet 571 of the magnetic force part 57 from the narrow diameter portion $211_ia$ of the dispensing tip $211_i$, the magnetic particles are stirred within the liquid, the NaCl and the SDS is removed, and the protein is washed. Thereafter, in a state in which the magnetic particles are adsorbed on the inner wall of the narrow diameter portion $211_ia$ by approaching the magnet 571 of the magnetic force part 57 to the narrow diameter portion $211_ia$ of the dispensing tip $211_i$ again, the dispensing tip $211_i$ is, following raising by means of the nozzle Z axis transfer mechanism 75, moved from the sixth liquid housing part to the seventh liquid housing part in which the distilled water is housed, by means of the nozzle head transfer mechanism 51.

In step S11, the narrow diameter portion $211_ia$ of the dispensing tip $211_i$ is lowered through the hole by means of the nozzle Z axis transfer mechanism 75, and by repeating the suction and the discharge of the water at a slow flow rate in a state where the magnetic force is applied within the narrow diameter portion $211_ia$ of the dispensing tip $211_i$, the isopropanol is substituted by water and is removed. Thereafter, by stirring the magnetic particles by repeating the suction and the discharge within the distilled water which represents the dissociation liquid, in a state in which the magnet 571 of the magnetic force part 57 is separated from the narrow diameter portion $211_ia$ of the dispensing tip $211_i$ and the magnetic force is removed, the nucleic acids or the fragments thereof retained by the magnetic particles are dissociated (eluted) from the magnetic particles into the liquid. Thereafter, a magnetic field is applied within the narrow diameter portion and the magnetic particles are adsorbed on the inner wall by approaching the magnet 571 to the narrow diameter portion $211_ia$ of the dispensing tip $211_i$, and the solution containing the extracted nucleic acids, and the like, is made to remain in the eighth liquid housing part. The dispensing tip $211_i$ is moved to the storage part of the housing parts for tips and the like $21_i$ in which the dispensing tip $211_i$ was housed, by means of the nozzle head transfer mechanism 51, and the dispensing tip $211_i$ to which magnetic particles are adsorbed, is detached from the nozzle $71_i$ together with the magnetic particles and dropped into the storage part, using the detaching member 591 of the tip detaching mechanism 59.

The following step S12 to step S15 corresponds to nucleic acid amplification and measurement processing.

In step S12, a new dispensing tip $211_i$ is mounted on the nozzle $71_i$, the solution housed within the eighth liquid housing part, which contains nucleic acids and the like, is aspirated, and by transferring it to the housing part for reactions $8_i$, in which the solution for amplification $8f_i$ is housed beforehand, and discharging it, it is introduced into the container. As a result of moving the nozzle head 50 by means of the nozzle head transfer mechanism 51, the nozzle $71_i$ is moved above the sealing lid housing part $8m_i$ of the container group 20, which houses the sealing lid $253_i$. Mounting is performed by lowering using the nozzle Z axis transfer mechanism 75 and fitting the cavity $253f$ on the upper side of the sealing lid 253 and fitting it to the lower end of the nozzle $71_i$. After being raised by the nozzle Z axis transfer mechanism 75, the sealing lid 253 is positioned above the housing part for reactions $8_i$ using the nozzle head transfer mechanism 51, and by lowering the sealing lid 253 by means of the nozzle Z axis transfer mechanism 75, it is fitted with the aperture of the wide-mouthed piping part $8a_i$ of the housing part for reactions $8_i$, mountingly sealing it.

In step S13, the nozzle head transfer mechanism 51 is instructed by means of an instruction from the measurement control portion, and by moving the nozzle head 50 along the X axis, the linking portion $31_i$ of the light guide stage 32 is positioned above the housing part for reactions $8_i$, which is mounted with the sealing lid $253_i$. Then, by lowering the light guide stage 32 by means of the stage Z axis transfer mechanism 35, the linking portion $31_i$ is inserted into the cavity $253f_i$ of the sealing lid $253_i$, and the lower end thereof is made to make contact with, or adhere to, the bottom surface $253g_i$ of the cavity.

In step S14, due to an instruction by the nucleic acid processing controller, the temperature controller 29 instructs a temperature control cycle by real-time PCR, such as a cycle in which the housing part for reactions $8_i$ is heated for five seconds at 96° C. and heated for 15 seconds at 60° C., to be repeated forty nine times for example.

In step S15, when temperature control at each cycle by the nucleic acid processing controller is started, the measurement control portion determines the start of elongation reaction processing at each cycle, and instructs the continuous or intermittent movement of the connecting end arranging body 30 with respect to the measuring ends $44_j$ of the measuring device 40. For the movement speed thereof, it is moved at a speed that is calculated based on the stable light receivable time, the fluorescence lifetime, and the number (twelve in this example) of exclusive regions $20_i$. Consequently, the receiving of light from all twelve housing parts for reactions $8_i$ within the stable light receivable time becomes completed.

In step S16, the measurement control portion determines the moment of each optical connection between the optical fibers (bundles) $33_i$ of the linking portions $31_i$ and the first measuring end and the second measuring end of the measuring end 44, and instructs the receiving of light to the measuring device 40 for example.

This measurement is executed with respect to cycles in which exponential amplification is performed, and an amplification curve is obtained based on the measurement, and various analyses are performed based on the amplification curve. At the time of the measurement, the measurement control portion heats the heater 37 built into the light guide stage 32 and prevents the condensation on the sealing lid 253, and a clear measurement can be performed.

The foregoing embodiments have been specifically described in order to better understand the present invention, and they are in no way limiting of other embodiments. Therefore, modifications are possible within a scope that does not depart from the gist of the invention. The configurations, shapes, materials, arrangements, and amounts of the nozzles, the dispensing tips, the punching tips, the container group, the exclusive regions thereof, the housing parts, the housing parts for reactions, the wide-mouthed piping part, the narrow-mouthed piping part, the measuring ends, the measuring devices, the specific wavelength measuring devices, the suction-discharge mechanism, the transfer mechanism portion, the magnetic force part, the heating portion, the reaction container, the sealing lids, the light guide stage, the linking portions, the light guide portions, the connecting ends, the connecting end arranging body, the linking portion arranging body, the nozzle head, the temperature controller, and the like, and the utilized reagents and samples are also in no way limited by the examples illustrated in the embodiments. Furthermore, although the nozzles were made to move with respect to the container group, it is possible to also move the container group with respect to the nozzles.

Furthermore, in the foregoing descriptions, although a sealing lid was used for the sealing of the housing part for reactions, it is possible, in its place or in combination, to perform sealing using a sealing liquid, such as mineral oil. Moreover, in place of punching by mounting a tip for punching on the nozzle, it is also possible to use a punching pin that is driven by the suction-discharge mechanism. Moreover, in the foregoing descriptions, although a real-time PCR measurement was described, it is in no way limited to this measurement, and it may also be applied to a variety of other measurements in which temperature control is performed. In the foregoing descriptions, although a case where the measuring device is provided to a dispensing device was described, it is not necessarily limited to this.

Furthermore, the devices described in the respective exemplary embodiments of the present invention, the components that form these devices, or the components that form these components, can be appropriately selected, and can be mutually combined by applying appropriate modifications. The spatial representations within the present application, such as "above, "below", interior", "exterior", "X axis", "Y axis", and "Z axis" are for illustration only, and are in no way limiting of the specific spatial directions or positions of the construction.

INDUSTRIAL APPLICABILITY

The present invention is related to fields in which the processing, testing, and analysis of nucleic acids, which primarily includes DNA, RNA, mRNA, rRNA, and tRNA for example, is required, and is related to industrial fields, agricultural fields such as food, agricultural products, and fishery processing, chemical fields, pharmaceutical fields, health care fields such as hygiene, insurance, diseases, and genetics, and scientific fields such as biochemistry or biology for example. The present invention is, in particular, able to be used in processing and analysis that handles various nucleic acids, and the like, such as PCR and real-time PCR.

BRIEF DESCRIPTION OF THE REFERENCE SYMBOLS 1, 3, 5, 8 Housing part for reactions
1a, 3a, 5a, 8a Wide-mouthed piping part
1b, 3b, 5b, 8b Narrow-mouthed piping part
1c, 3c, 5c, 8c Punchable film
1f, 3f, 5f, 8f Reaction reagent
2, 4, 6, 7, 9, 201 Reaction container
10 Reaction container light measurement device
20 Container group
$20_i$ (i=1, . . . , 12) Exclusive regions 211$_i$ (i=1, ..., 12) Dispensing tip
212 Tip for punching
231$_i$, 236$_i$ (i=1, ..., 12) PCR tube (reaction container)
251, 252, 253 Sealing lid
251a, 252a, 253a Plug portion
251b, 252b, 253b Protrusion
251c, 252c, 253c Cylindrical member
251d, 252d, 252d Pushing portion
251e, 252e, 252e Circular protrusion
251f, 252f, 253f Cavity
251g, 252g, 253g Bottom of cavity
252h O ring
253h Circular protrusion
29 Temperature controller
30 Connecting end arranging body
31$_i$, 141$_i$ (i=1, ..., 12) Linking portion
32 Light guide stage
33$_i$, 142$_i$ Optical fiber (light guide portion)
40, 140 Measuring device
40$_j$ (j=1, ..., 6) Specific wavelength measuring device
44 Measuring end
50 Nozzle head
52 Transfer mechanism portion
53 Suction-discharge mechanism
59 Tip detaching mechanism
70 Nozzle arranging portion
71$_i$ (i=1, ..., 12) Nozzles

The invention claimed is:

1. A reaction container comprising:
one or two or more housing parts for reactions comprising: a narrow-mouthed piping part formed with a rotation symmetry and in which a reaction reagent or a portion thereof is housed or is housable; a wide-mouthed piping part that is communicated with the narrow-mouthed piping part and provided on an upper side of the narrow-mouthed piping part, the wide-mouthed piping part being formed with a rotation symmetry coaxially with the narrow-mouthed piping part and having an aperture that is wider than an aperture of said narrow-mouthed piping part; and a punchable film provided such that it partitions an interval between the wide-mouthed piping part and the narrow-mouthed piping part, the punchable film, when punched, being insertable into the aperture of said narrow-mouthed piping part; and
a sealing lid that seals the reaction container by being mounted on the aperture of said wide-mouthed piping part of said reaction container, said sealing lid comprising: a plug portion defining an internal cavity and an exterior bottom surface having transparency, wherein the plug portion is fittable to an inside wall defined by the aperture of said wide-mouthed piping part and is able to guide light from said narrow-mouthed piping part; and a pushing portion provided to the exterior bottom surface of said plug portion so that, after the film has been punched and during the fitting of the plug portion with the wide-mouthed piping part, the pushing portion pushes said film, which has been already punched, into the aperture of the narrow-mouthed piping part, and against an inner wall of the narrow-mouthed piping part, thus enabling the plug portion to guide light from said narrow-mouthed piping part;
wherein the pushing portion comprises a cylindrical wall extending vertically downward from the exterior bottom surface of the sealing lid and formed so as to circularly enclose a center portion, through which the light guided by the sealing lid passes, adjacent the exterior bottom surface, which exterior bottom surface encloses the center portion at one end of the cylindrical wall to separate the center portion from the internal cavity of the plug portion;
wherein, when the plug portion is fitted to the inside wall defined by the aperture of the wide-mouthed piping part, at least a portion of the pushing portion extends downward into the narrow-mouthed piping part and an annular region is defined between an exterior surface of the cylindrical wall of the pushing portion and the inner wall of the narrow-mouthed piping part, so that no portion of the exterior surface contacts the inner wall at any location between the exterior bottom surface of the plug portion and a bottom end of the pushing portion; and
wherein the cylindrical wall of the pushing portion extends vertically downward from the exterior bottom surface of the sealing lid by a vertical length that is longer than a radial length of the annular region so that, when the plug portion is fitted to the inside wall defined by the aperture of the wide-mouthed piping part, the cylindrical wall of the pushing portion extends downward to push said punched film into the aperture of the narrow-mouthed piping part and against the inner wall of the narrow-mouthed piping part.

2. A reaction container according to claim 1, in which the aperture of said narrow-mouthed piping part is provided at the center of a bottom portion of the wide-mouthed piping part.

3. A reaction container according to claim 1, wherein said narrow-mouthed piping part and said wide-mouthed piping part are integrally formed, and said film is attached to a bottom portion of said wide-mouthed piping part.

4. A reaction container according to claim 1 that has a cartridge container which further has a base plate in which two or more concave portions are arranged in a single row form, and said housing part for reactions is formed in one of the concave portions, and in the other of the concave portions excluding the concave portion in which said housing part for reactions is formed, instruments for performing processing that are moved to said housing part for reactions are housed or are housable.

5. A reaction container according to claim 4, wherein said other concave portions excluding the concave portion in which said housing part for reactions is formed, are provided with a sealing lid housing part that houses said sealing lid, a tip for punching housing part that houses a tip for punching that punches said film, and/or a dispensing tip housing part that houses a dispensing tip.

6. A reaction container according to claim 4, wherein said wide mouth piping part of said container for reaction formed in said concave portion comprises a concave portion having an aperture formed in said base plate, and said narrow-mouthed piping part is separately formed from said wide-mouthed piping part, a hole portion is piercingly provided in the center of a bottom portion of the wide-mouthed piping part, said narrow-mouthed piping part has an aperture edge portion that encloses the aperture thereof, said narrow-mouthed piping part downwardly protrudes from said hole portion of the wide-mouthed piping part such that it passes through said hole portion, said aperture edge portion is installed on the bottom portion of said wide-mouthed piping part, and said film is attached to said aperture edge portion of said narrow-mouthed piping part.

7. A reaction container according to claim 1, wherein said wide-mouthed piping part or said sealing lid are adapted to be able to be linked with a linking portion, the linking portion including ends of one or two or more light guide portions so that, when the linking portion is linked with said wide-mouthed piping part or said sealing lid, the light guide portions optically connect a light measuring device provided on the exterior of the reaction container with the interior of the housing part for reactions.

8. A reaction container according to claim 1, wherein said sealing lid has: a cavity provided in the center thereof; and a bottom surface, which has transparency, that blocks a lower end of the cavity, and movement of the sealing lid to the housing part for reactions, and the fitting and/or the linking with said linking portion, is performed by inserting a member provided on the exterior of the reaction container and/or said linking portion into said cavity.

9. A reaction container comprising:
one or two or more housing parts for reactions comprising: a narrow-mouthed piping part formed with a rotation symmetry and in which a reaction reagent or a portion thereof is housed or is housable; a wide-mouthed piping part that is communicated with the narrow-mouthed piping part and provided on an upper side of the narrow-mouthed piping part, the wide-mouthed piping part being formed with a rotation symmetry coaxially with the narrow-mouthed piping part and having an aperture that is wider than an aperture of said narrow-mouthed piping part; and a punchable film provided such that it partitions an interval between the wide-mouthed piping part and the narrow-mouthed piping part, the punchable film, when punched, being insertable into the aperture of said narrow-mouthed piping part; and a sealing lid that seals the reaction container by being mounted on the aperture of said wide-mouthed piping part of said reaction container, said sealing lid comprising: a plug portion defining an internal cavity and an exterior bottom surface having transparency, wherein the plug portion is fittable to an inside wall defined by the aperture of said wide-mouthed piping part and is able to guide light from said narrow-mouthed piping part; and a pushing portion provided to the exterior bottom surface of said plug portion so that, after the film has been punched and during the fitting of the plug portion with the wide-mouthed piping part, the pushing portion pushes said film, which has been already punched, into the aperture of the narrow-mouthed piping part, and against an inner wall of the narrow-mouthed piping part, thus enabling the plug portion to guide light from said narrow-mouthed piping part;

wherein said wide-mouthed piping part and said narrow-mouthed piping part are separately formed, said wide-mouthed piping part having a hole portion piercingly provided in the center of a bottom portion thereof, said narrow-mouthed piping part having an aperture edge portion provided along an outer circumference of the aperture thereof, so as to enclose the aperture, and said film being attached to said aperture edge portion;

wherein, excluding for said aperture edge portion, the narrow-mouthed piping part is able to pass through said hole portion such that said aperture edge portion is installed on the bottom of said wide-mouthed piping part and said narrow-mouthed piping part downwardly protrudes from said hole portion of said wide-mouthed piping part;

wherein the pushing portion comprises a cylindrical wall extending vertically downward from the exterior bottom surface of the sealing lid and formed so as to circularly enclose a center portion, through which the light guided by the sealing lid passes, adjacent the exterior bottom surface, which exterior bottom surface encloses the center portion at one end of the cylindrical wall to separate the center portion from the internal cavity of the plug portion;

wherein, when the plug portion is fitted to the inside wall defined by the aperture of the wide-mouthed piping part, at least a portion of the pushing portion extends downward into the narrow-mouthed piping part and an annular region is defined between an exterior surface of the cylindrical wall of the pushing portion and the inner wall of the narrow-mouthed piping part, so that no portion of the exterior surface contacts the inner wall at any location between the exterior bottom surface of the plug portion and a bottom end of the pushing portion; and wherein the cylindrical wall of the pushing portion extends vertically downward from the exterior bottom surface of the sealing lid by a vertical length that is longer than a radial length of the annular region so that, when the plug portion is fitted to the inside wall defined by the aperture of the wide-mouthed piping part, the cylindrical wall of the pushing portion extends downward to push said punched film into the aperture of the narrow-mouthed piping part and against the inner wall of the narrow-mouthed piping part.

10. A reaction container according to claim 9, wherein said wide-mouthed piping part or said sealing lid are adapted to be able to be linked with a linking portion, the linking portion including ends of one or two or more light guide portions so that, when the linking portion is linked with said wide-mouthed piping part or said sealing lid, the light guide portions optically connect a light measuring device provided on the exterior of the reaction container with the interior of the housing part for reactions.

11. A reaction container according to claim 10, wherein said sealing lid has a cavity provided in the center thereof, wherein the exterior bottom surface, which has transparency, blocks a lower end of the cavity, and movement of the sealing lid to the housing part for reactions, and the fitting and/or the linking with said linking portion, is performed by inserting a member provided on the exterior of the reaction container and/or said linking portion into said cavity.

12. A reaction container according to claim 9 that has a cartridge container which further has a base plate in which two or more concave portions are arranged in a single row form, and said housing part for reactions is formed in one of the concave portions, and in the other of the concave portions excluding the concave portion in which said housing part for reactions is formed, instruments for performing processing that are moved to said housing part for reactions are housed or are housable.

13. A reaction container according to claim 12, wherein said other concave portions excluding the concave portion in which said housing part for reactions is formed, are provided with a sealing lid housing part that houses said sealing lid, a tip for punching housing part that houses a tip for punching that punches said film, and/or a dispensing tip housing part that houses a dispensing tip.

14. A reaction container according to claim 12, wherein said wide mouth piping part of said container for reaction formed in said concave portion comprises a concave portion having an aperture formed in said base plate.

15. A method
comprising:

providing a narrow-mouthed piping part of a reaction container in which a reaction reagent or a portion thereof is housed or is housable, the narrow-mouthed piping part including a first aperture and an aperture edge portion provided along an outer circumference of the first aperture, attaching a punchable film to said aperture edge portion of said narrow-mouthed piping part so that the punchable film, when punched, is insertable into the first aperture, providing a wide-mouthed piping part of the reaction container including a second aperture and a hole portion piercingly provided in a center of a bottom portion of the wide-mouthed piping part, the second aperture being wider than the first aperture, passing said narrow-mouthed piping part, excluding the aperture edge portion, through said hole portion of the wide-mouthed piping part such that said aperture edge portion is installed on the bottom portion of said wide-mouthed piping part and at least part of the narrow-mouthed piping part downwardly protrudes from the hole portion of the wide-mouthed piping part, punching the punchable film, and sealing the reaction container by mounting a sealing lid on the second aperture, the sealing lid comprising:
- a plug portion defining an internal cavity and an exterior bottom surface having transparency,
  - wherein mounting the sealing lid on the second aperture fits the plug portion to an inside wall defined by the second aperture so that the sealing lid is able to guide light from the narrow-mouthed piping part via at least the exterior bottom surface, and
- a pushing portion extending from the exterior bottom surface of the plug portion,
  - wherein mounting the sealing lid on the second aperture causes the pushing portion to push the punched film into the first aperture and against an inner wall of the narrow-mouthed piping part, thus enabling the plug portion to guide light from the narrow-mouthed piping part,
  - wherein the pushing portion comprises a wall extending from the exterior bottom surface of the sealing lid and formed so as to circularly enclose a center portion, through which the light guided by the sealing lid passes, adjacent the exterior bottom surface,
  - wherein the exterior bottom surface separates the center portion from the internal cavity of the plug portion,
  - wherein fitting the plug portion to the inside wall defined by the second aperture extends at least part of the pushing portion downward into the narrow-mouthed piping part so that an annular region is defined between an exterior surface of the wall of the pushing portion and the inner wall of the narrow-mouthed piping part,
  - wherein no portion of the exterior surface contacts the inner wall at any location between the exterior bottom surface of the plug portion and a bottom end of the pushing portion, and
  - wherein the wall of the pushing portion extends from the exterior bottom surface of the sealing lid by a vertical length that is longer than a radial length of the annular region so that fitting the plug portion to the inside wall defined by the second aperture extends the pushing portion downward to push said punched film into the first aperture of the narrow-mouthed piping part and against the inner wall of the narrow-mouthed piping part.

16. A system, comprising:
a nozzle head provided with a suction-discharge mechanism and two or more nozzles to which dispensing tips are detachably mountable, wherein suction and discharge of liquids is possible using the suction-discharge mechanism and the nozzles;

a container group including two or more reaction containers in which a solution for reaction is housed or is housable;

a nozzle transfer mechanism adapted to relatively move said nozzle head and/or said container group;

a temperature controller adapted to control an interior temperature of said reaction containers;

a light guide stage including two or more linking portions that are directly or indirectly linkable with said reaction containers, wherein respective first ends of two or more light guide portions are provided to the linking portions so that, when the linking portions are directly or indirectly linked with the reaction containers, the light guide portions are optically connected with the respective interiors of the linked reaction containers;

a connecting end arranging body including an arranging surface that supports two or more connecting ends along a predetermined path, wherein respective second ends of said light guide portions are provided to the connecting ends;

a measuring device provided adjacent said arranging surface so that, by means of optical connections with the respective connecting ends, the measuring device is able to receive light based on optical states within said reaction containers, wherein the measuring device and/or said respective connecting ends are relatively movable such that the measuring device is successively optically connected to the respective connecting ends, wherein each of the reaction containers comprises:
- a narrow-mouthed piping part in which a reaction reagent is housed or is housable, the narrow-mouthed piping part including a first aperture;
- a wide-mouthed piping part that is communicated with the narrow-mouthed piping part and provided on an upper side of the narrow-mouthed piping part, the wide-mouthed piping part including a second aperture that is wider than the first aperture of said narrow-mouthed piping part; and
- a punchable film provided such that it partitions an interval between the wide-mouthed piping part and the narrow-mouthed piping part, the punchable film, when punched, being insertable into the first aperture of the narrow-mouthed piping part, and wherein the linking portions are linkable with the reaction containers via sealing lids, each of the sealing lids comprising:
- a plug portion defining an internal cavity and an exterior bottom surface having transparency,
  - wherein the plug portion is fittable to an inside wall defined by the second aperture and is able to guide light from the narrow-mouthed piping part, and
- a pushing portion extending from the exterior bottom surface of the plug portion so that, after the punchable film has been punched and during fitting of the plug portion with the wide-mouthed piping part, the pushing portion pushes the punched film into the first aperture and against an inner wall of the narrow-mouthed piping part, thus enabling the plug portion to guide light from the narrow-mouthed piping part, wherein the pushing portion comprises a wall extending from the exterior bottom surface of the sealing lid and formed so as to circularly enclose a center portion, through which the light guided by the sealing lid passes, adjacent the exterior bottom surface, wherein the exterior bottom surface separates the center portion from the internal cavity of the plug portion, wherein, when the plug portion is fitted to the inside wall defined by the second aperture, at least part of the pushing portion extends downward into the narrow-mouthed piping part and an annular region is defined between an exterior surface of the wall of the pushing portion and the inner wall of the narrow-mouthed piping part, so that no portion of the exterior surface contacts the inner wall at any location between the exterior bottom surface of the plug portion and a bottom end of the pushing portion, and wherein the wall of the pushing portion extends vertically downward from the exterior bottom surface of the sealing lid by a vertical length that is longer than a radial length of the annular region so that, when the plug portion is fitted to the inside wall defined by the second aperture of the wide-mouthed piping part, the wall of the pushing portion extends downward to push said punched film into the first aperture and against the inner wall of the narrow-mouthed piping part.

17. A reaction container system according to claim 16, wherein said container group additionally has: two or more liquid housing parts that house; a sample, a magnetic particle suspension in which magnetic particles that are able to capture a target substance of a reaction are suspended, and a solution for separating and extracting used for the separation and the extraction of said target substance; and a magnetic force part that is able to apply or remove a magnetic field to the interior of said dispensing tips mounted on said nozzles or the liquid housing parts provided to said container group, and which is able to adsorb said magnetic particles on an inner wall of said dispensing tips or said liquid housing parts.

18. A reaction container, comprising:
a housing part, comprising:
a narrow-mouthed piping part formed with a rotation symmetry and in which a reaction reagent or a portion thereof is housed or is housable, the narrow-mouthed piping part comprising:
a frusto-conically-shaped wall, the frusto-conically-shaped wall extending angularly downward, the frusto-conically shaped wall defining a frusto-conical inside surface;
a bottom wall to which the frusto-conically-shaped wall extends, the bottom wall defining a bottom inside surface that is contiguous with the frusto-conical inside surface,
wherein the frusto-conical inside surface and the bottom inside surface at least partially define a first internal region in which the reaction reagent or a portion thereof is housed or is housable;
an intermediate portion connected to the frusto-conically-shaped wall and from which the frusto-conically-shaped wall extends angularly downward,
wherein the intermediate portion is formed with a rotation symmetry coaxially with the narrow-mouthed piping part and defines a first circular opening circumscribed by the frusto-conical inside surface at the connection between the intermediate portion and the frusto-conically-shaped wall;
wherein the first circular opening has a first diameter;
wherein the intermediate portion defines an annular horizontally-extending inside surface and an annular rounded inside surface extending therefrom,
wherein the annular rounded inside surface also circumscribes the first circular opening of the intermediate portion;
wherein the annular rounded inside surface extends from the annular horizontally-extending inside surface to the frusto-conical inside surface; and
wherein the annular horizontally-extending inside surface, the annular rounded inside surface, the frusto-conical inside surface, and the bottom inside surface are contiguous;
and
a first cylindrical wall extending upward and opposite the downward extension of the frusto-conically-shaped wall, the first cylindrical wall being formed with a rotation symmetry coaxially with the narrow-mouthed piping part and defining a first cylindrical vertically-extending inside surface that is perpendicular to the annular horizontally-extending inside surface;
wherein the first cylindrical wall defines a second circular opening, the second circular opening having a second diameter that is greater than the first diameter of the first circular opening; and
wherein the first cylindrical vertically-extending surface and the annular horizontally-extending inside surface at least partially define a second internal region;
a sealing lid, comprising:
a plug portion that extends through the second circular opening and within the second internal region, the plug portion comprising:
a second cylindrical wall, the second cylindrical wall defining a first outside surface that contacts the first cylindrical vertically-extending inside surface of the housing part, the second cylindrical wall further defining a second vertically-extending inside surface; and
a circular horizontally-extending end cap connected to the lower end of the second cylindrical wall;
wherein the circular horizontally-extending end cap is transparent;
wherein the circular horizontally-extending end cap defines a circular inside surface; and
wherein the second vertically-extending inside surface and the circular inside surface at least partially define an internal cavity;
and
a pushing portion connected to the plug portion, the pushing portion comprising a third cylindrical wall extending vertically downward from the circular horizontally-extending end cap of the plug portion and into the first circular opening, the third cylindrical wall being formed so as to circularly enclose a center portion, through which light guided by the sealing lid passes, adjacent the circular horizontally-extending end cap, which circular horizontally-extending end cap encloses the center portion at one end of the cylindrical wall to separate the center portion from the internal cavity of the plug portion;
   wherein the third cylindrical wall defines a third diameter that is less than the first diameter of the first circular opening so that the third cylindrical wall of the pushing portion is able to extend into the first circular opening of the housing part, and
   wherein the third cylindrical wall of the pushing portion extends downward into the narrow-mouthed piping part, and an annular region is defined between an exterior surface of the third cylindrical wall and the frusto-conical inside surface defined by the frusto-conically shaped wall of the narrow-mouthed piping part, so that no portion of the exterior surface contacts the frusto-conical inside surface at any location between the circular horizontally-extending end cap of the plug portion and a bottom end of the pushing portion;

and a film positioned between the housing part and the sealing lid so that:
   the film extends between the annular horizontally-extending inside surface of the housing part and the circular horizontally-extending end cap of the sealing lid;
   an opening is defined in the film due to the extension of the third cylindrical wall into the first circular opening; and
   the film extends between the annular rounded inside surface of the housing part and the third cylindrical wall of the plug portion of the sealing lid;
wherein the housing part, the sealing lid, and the film are configured so that the plug portion is able to guide light:
   from the first internal region of the narrow-mouthed piping part of the housing part,
   vertically along the third cylindrical wall of the pushing portion of the sealing lid,
   through the transparent circular horizontally-extending end cap of the plug portion of the sealing lid, and
   into the internal cavity of the sealing lid; and
wherein the third cylindrical wall of the pushing portion extends vertically downward from the circular horizontally-extending end cap of the plug portion by a vertical length that is longer than a radial length of the annular region so that the third cylindrical wall of the pushing portion extends downward to push said film into the first circular opening of the intermediate portion and against the frusto-conical wall of the narrow-mouthed piping part.

19. The reaction container of claim 18, wherein the narrow-mouthed piping part, the intermediate portion, and the first cylindrical wall of the housing part are integrally formed.

* * * * *